United States Patent
Fan

(10) Patent No.: US 9,474,438 B2
(45) Date of Patent: Oct. 25, 2016

(54) CONTINUOUS FLOW ENDOSCOPE SYSTEMS

(75) Inventor: Tailin Fan, Nashua, NH (US)

(73) Assignee: GYRUS ACMI, Inc., Southborough, MA (US)

(*) Notice: Subject to any disclaimer, the term of this patent is extended or adjusted under 35 U.S.C. 154(b) by 393 days.

(21) Appl. No.: 13/115,855

(22) Filed: May 25, 2011

(65) Prior Publication Data
US 2011/0295066 A1    Dec. 1, 2011

Related U.S. Application Data

(60) Provisional application No. 61/349,805, filed on May 28, 2010.

(51) Int. Cl.
| A61B 1/04 | (2006.01) |
| A61B 1/018 | (2006.01) |
| A61B 1/00 | (2006.01) |
| A61B 1/015 | (2006.01) |
| A61B 18/14 | (2006.01) |

(Continued)

(52) U.S. Cl.
CPC .......... *A61B 1/018* (2013.01); *A61B 1/00119* (2013.01); *A61B 1/00128* (2013.01); *A61B 1/015* (2013.01); *A61B 18/149* (2013.01); *A61B 18/1482* (2013.01); *A61B 2018/00029* (2013.01); *A61B 2018/00196* (2013.01); *A61B 2018/1213* (2013.01); *A61B 2217/005* (2013.01); *A61B 2218/002* (2013.01); *A61B 2218/007* (2013.01)

(58) Field of Classification Search
USPC ....... 600/105, 114, 128, 130, 134, 137, 153, 600/154, 156
See application file for complete search history.

(56) References Cited

U.S. PATENT DOCUMENTS 2,487,502 A * 11/1949 Willinsky ........................ 606/46
3,186,924 A *  6/1965 Williamson .................. 202/173
(Continued)

FOREIGN PATENT DOCUMENTS

| EP | 1469771 | 10/2004 |
| JP | S56-113501 | 9/1981 |

(Continued)

OTHER PUBLICATIONS

Exam Report regarding European Patent Application No. 03 729 358.6, dated Dec. 11, 2006; (4 pages total).

(Continued)

*Primary Examiner* — Jae Woo
(74) *Attorney, Agent, or Firm* — The Dobrusin Law Firm, P.C.

(57) ABSTRACT

Endoscopes having a hollow outer sheath configured for insertion into a patient's body are disclosed. A hollow inner sheath is receivable within the outer sheath, and is configured to slideably receive a first internal instrument. A working element can be configured to rotatably support at least the first internal instrument and a second internal instrument such that at least the first internal instrument and the second internal instrument are rotatable about a common axis of rotation being substantially coextensive with a longitudinal axis of the outer sheath. The working element can have at least one guide rail extending longitudinally of the axis of rotation and an actuator block can be slideably mountable to the at least one guiderail and so securable to at least one of the instruments as to be able to urge the at least one of the internal instruments longitudinally of the outer sheath.

17 Claims, 17 Drawing Sheets

(51) Int. Cl.
*A61B 18/00* (2006.01)
*A61B 18/12* (2006.01)

(56) References Cited

U.S. PATENT DOCUMENTS

| | | | |
|---|---|---|---|
| 3,834,842 A | 9/1974 | Dorff et al. | |
| 3,835,842 A * | 9/1974 | Iglesias | 600/105 |
| 3,850,175 A | 11/1974 | Iglesias | |
| 4,066,330 A | 1/1978 | Jones | |
| 4,132,227 A * | 1/1979 | Ibe | 600/105 |
| 4,149,538 A * | 4/1979 | Mrava et al. | 606/46 |
| 4,726,370 A | 2/1988 | Karasawa et al. | |
| 4,769,018 A | 9/1988 | Wilson | |
| 4,852,550 A | 8/1989 | Koller et al. | |
| 4,867,138 A * | 9/1989 | Kubota et al. | 600/107 |
| 4,919,129 A * | 4/1990 | Weber et al. | 606/42 |
| 4,920,961 A * | 5/1990 | Grossi et al. | 606/14 |
| 4,959,058 A | 9/1990 | Michelson | |
| 5,112,330 A * | 5/1992 | Nishigaki et al. | 600/143 |
| 5,166,787 A | 11/1992 | Irion | |
| 5,197,963 A * | 3/1993 | Parins | 606/46 |
| 5,197,964 A | 3/1993 | Parins | |
| 5,287,845 A * | 2/1994 | Faul et al. | 600/135 |
| 5,320,091 A * | 6/1994 | Grossi et al. | 600/104 |
| 5,322,503 A | 6/1994 | Desai | |
| 5,392,765 A * | 2/1995 | Muller | 600/108 |
| 5,458,598 A | 10/1995 | Feinberg et al. | |
| 5,486,155 A * | 1/1996 | Muller et al. | 600/137 |
| 5,505,710 A * | 4/1996 | Dorsey, III | 604/158 |
| 5,509,892 A * | 4/1996 | Bonnet | 600/156 |
| 5,549,541 A * | 8/1996 | Muller | 600/105 |
| 5,662,647 A | 9/1997 | Crow et al. | |
| 5,662,680 A | 9/1997 | Desai | |
| 5,688,222 A * | 11/1997 | Hluchy et al. | 600/156 |
| 5,772,257 A * | 6/1998 | Webb et al. | 285/112 |
| 5,807,240 A * | 9/1998 | Muller et al. | 600/135 |
| 5,857,962 A * | 1/1999 | Bracci et al. | 600/105 |
| 5,934,682 A * | 8/1999 | Miszczak et al. | 277/313 |
| 5,972,002 A | 10/1999 | Bark et al. | |
| 5,976,129 A | 11/1999 | Desai | |
| 6,142,931 A * | 11/2000 | Kaji | 600/114 |
| 6,261,294 B1 | 7/2001 | Stihl et al. | |
| 6,358,200 B1 * | 3/2002 | Grossi | 600/156 |
| 6,471,684 B2 | 10/2002 | Dulak et al. | |
| 6,572,537 B2 | 6/2003 | Futatsugi et al. | |
| 6,579,224 B1 | 6/2003 | Burton et al. | |
| 6,579,277 B1 | 6/2003 | Rabiner et al. | |
| 6,641,530 B2 | 11/2003 | Mitsumori | |
| 6,648,816 B2 | 11/2003 | Irion et al. | |
| 6,712,759 B2 | 3/2004 | Muller et al. | |
| 6,824,544 B2 * | 11/2004 | Boebel et al. | 606/46 |
| 6,893,441 B2 * | 5/2005 | Brommersma et al. | 606/46 |
| 7,488,318 B2 * | 2/2009 | Aue et al. | 606/46 |
| 8,118,729 B2 * | 2/2012 | Hipp et al. | 600/105 |
| 8,475,362 B2 * | 7/2013 | Sohn et al. | 600/114 |
| 2001/0026666 A1 | 10/2001 | Ferrera et al. | |
| 2002/0058859 A1 | 5/2002 | Brommersma | |
| 2003/0220542 A1 * | 11/2003 | Belson et al. | 600/109 |
| 2004/0015045 A1 | 1/2004 | Burton et al. | |
| 2005/0228361 A1 | 10/2005 | Tremaglio | |
| 2006/0015007 A1 * | 1/2006 | Aue et al. | 600/105 |
| 2006/0122459 A1 * | 6/2006 | Aue | 600/105 |
| 2011/0144429 A1 | 6/2011 | Finkman et al. | |

FOREIGN PATENT DOCUMENTS

| | | |
|---|---|---|
| JP | 58-081029 | 5/1983 |
| JP | 61-159953 A | 7/1986 |
| JP | 61-185239 A | 8/1986 |
| JP | 62-144630 A | 6/1987 |
| JP | 63-135158 A | 6/1988 |
| JP | H02-224755 | 5/1989 |
| JP | 03-295550 A | 12/1991 |
| JP | 05-199983 A | 8/1993 |
| JP | 05-168643 | 2/1994 |
| JP | 09-262245 A | 10/1997 |
| JP | 2005-525144 | 8/2005 |
| JP | 2008-093019 | 4/2008 |
| JP | 4-290013 | 7/2009 |
| WO | 96/02182 | 2/1996 |
| WO | 03/057020 | 7/2003 |
| WO | 2011/081754 | 7/2011 |
| WO | 2011-150111 A1 | 12/2012 |

OTHER PUBLICATIONS

Exam Report regarding European Patent Application No. 03 729 358.6, dated Apr. 14, 2008; (6 pages total).

Exam Report regarding European Patent Application No. 03 729 358.6, dated Dec. 1, 2009; (7 pages total).

Office Action concerning Japanese Patent Application No. 2003-557388, dated Apr. 22, 2008; (4 pages total with English translation).

Japanese Patent Office Action dated Mar. 9, 2015 regarding Application No. 2013/512219.

International Preliminary Report, application No. PCT/US2011/037978 dated Dec. 13, 2012.

Japanese Office Action dated Jan. 4, 2016 regarding Application No. 2013/512219.

PCT International Search Report and Written Opinion concerning International Application No. PCT/US2011/037978, dated Sep. 22, 2011; (11 pages total).

PCT International Search Report concerning International Application No. PCT/US03/00359, dated Jun. 5, 2003; (5 pages total).

PCT Written Opinion from the International Preliminary Examining Authority concerning International Application No. PCT/US03/00359, dated Jan. 16, 2004; (5 pages total).

PCT International Preliminary Examination Report from the International Preliminary Examining Authority concerning International Application No. PCT/US03/00359, dated Oct. 12, 2004; (7 pages total).

Office Action relating to U.S. Appl. No. 10/041,645, dated Apr. 3, 2003; (8 pages total).

Office Action relating to U.S. Appl. No. 10/041,645, dated Aug. 8, 2003; (8 pages total).

\* cited by examiner

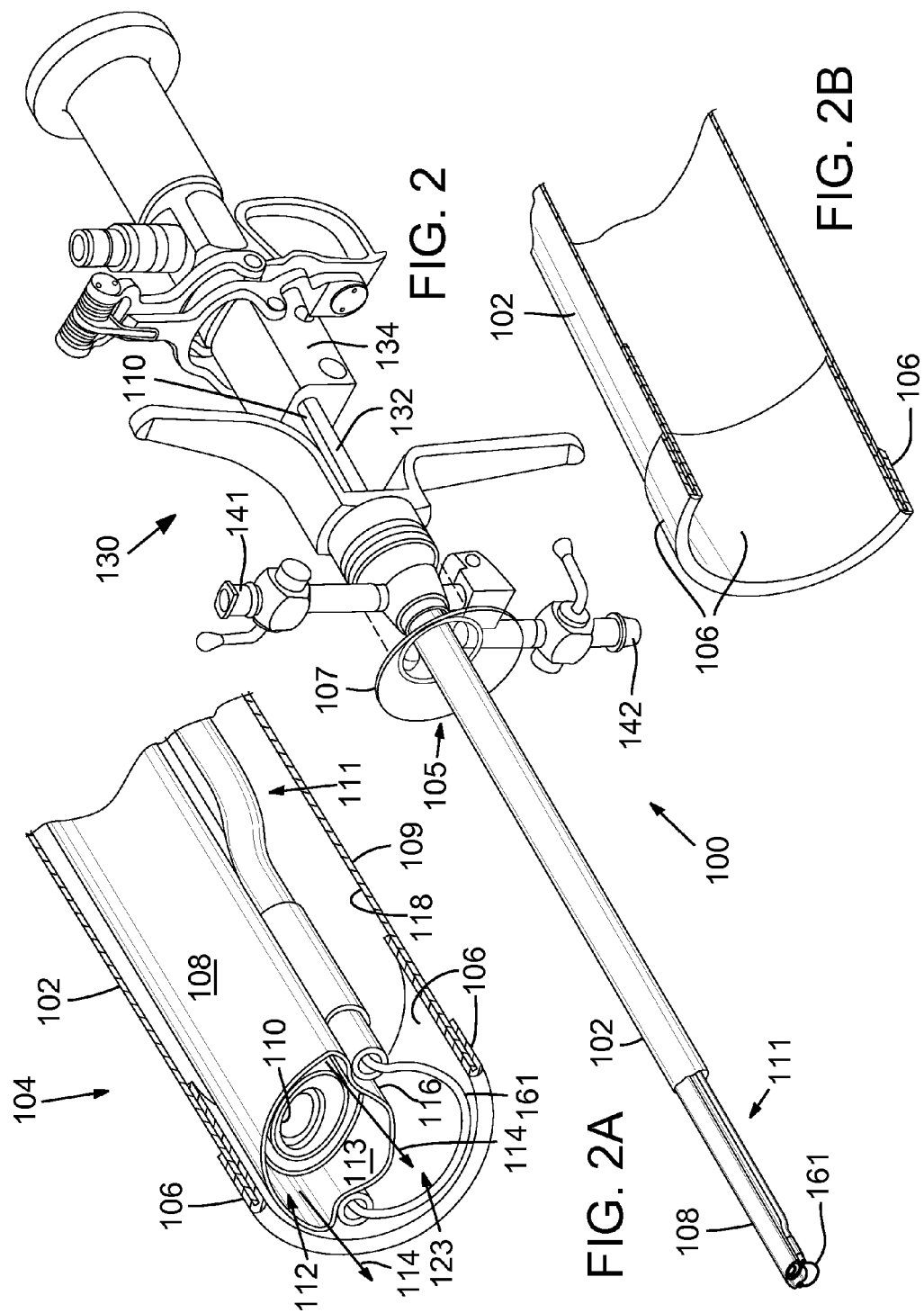

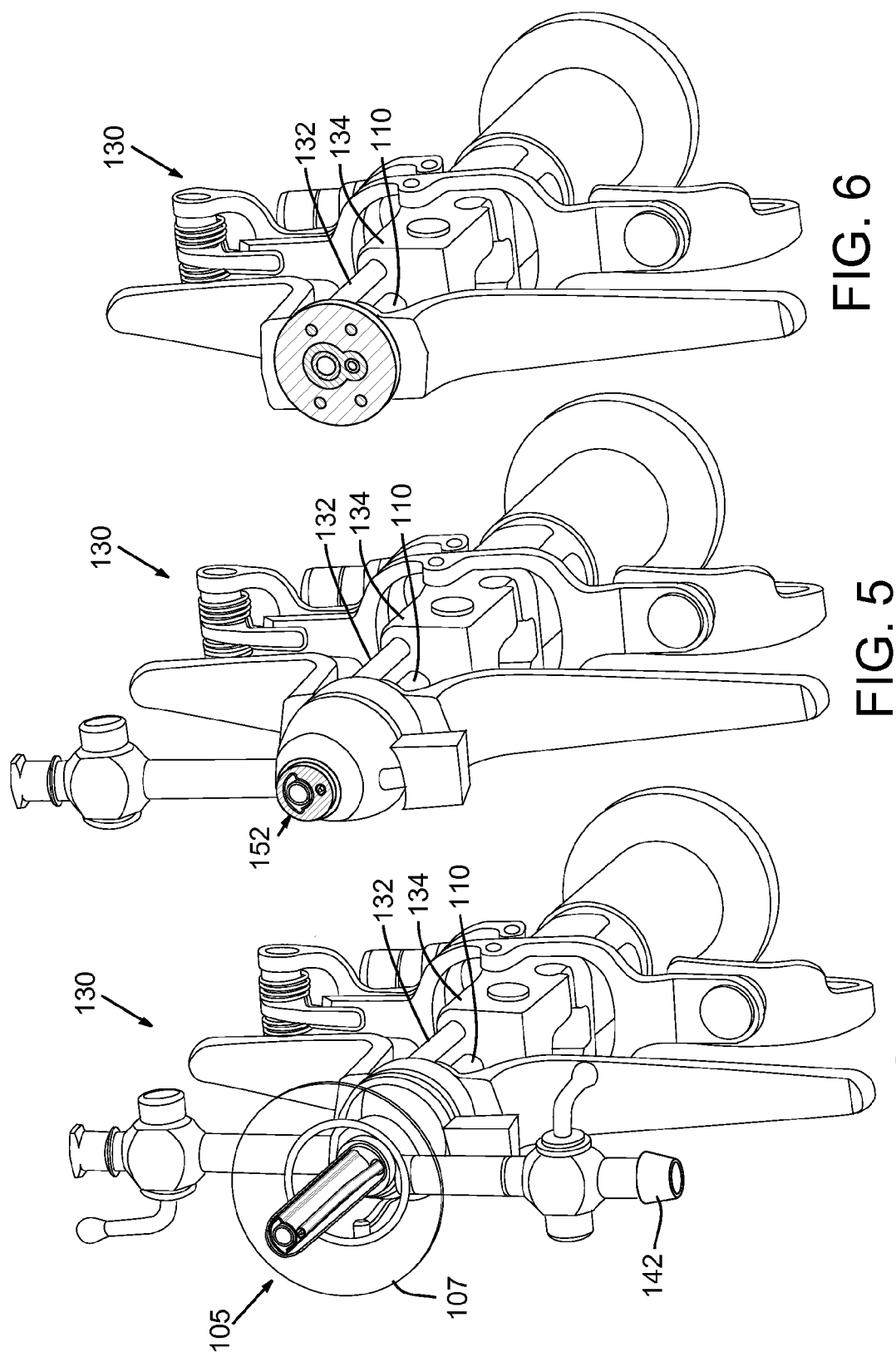

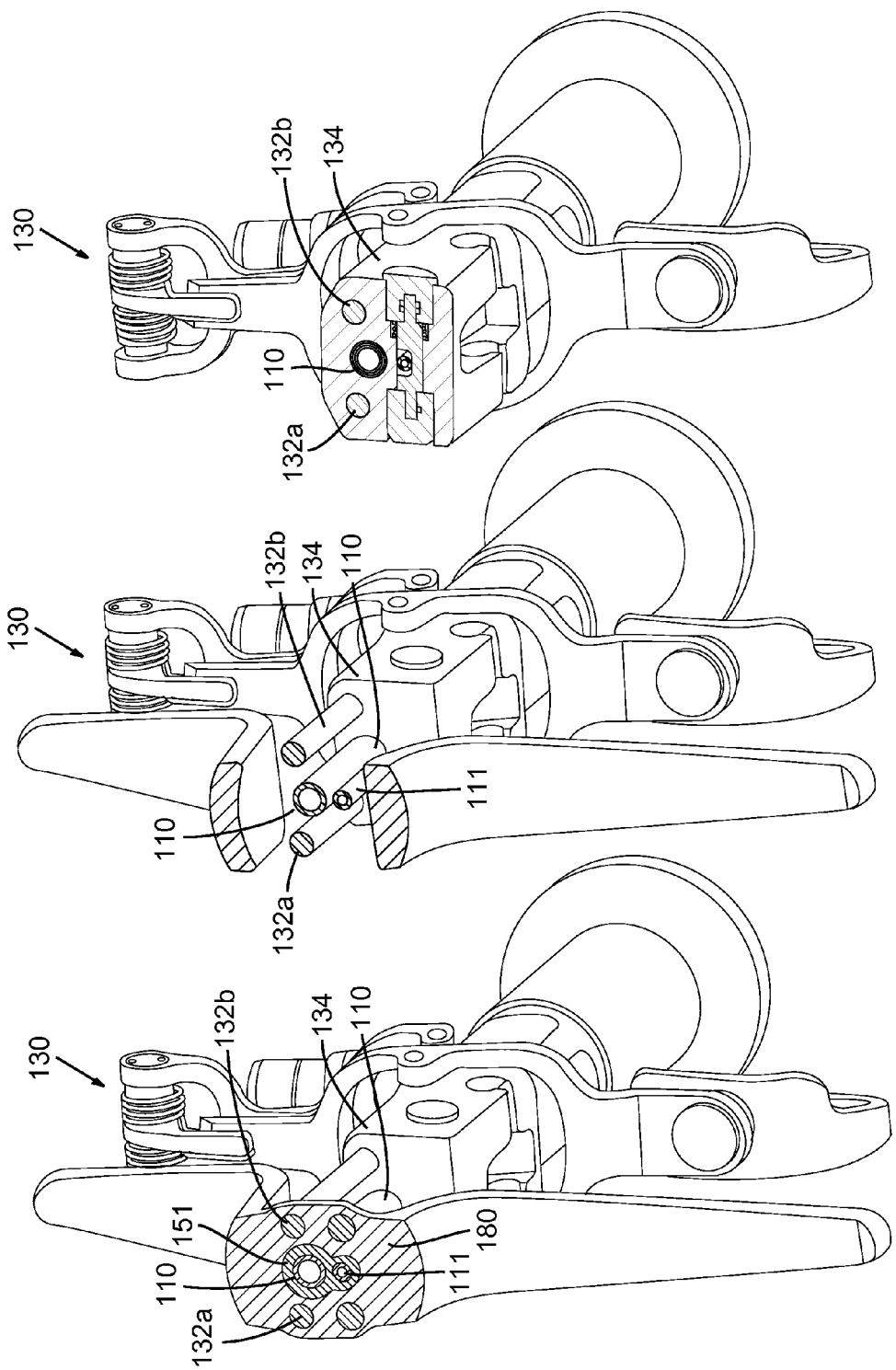

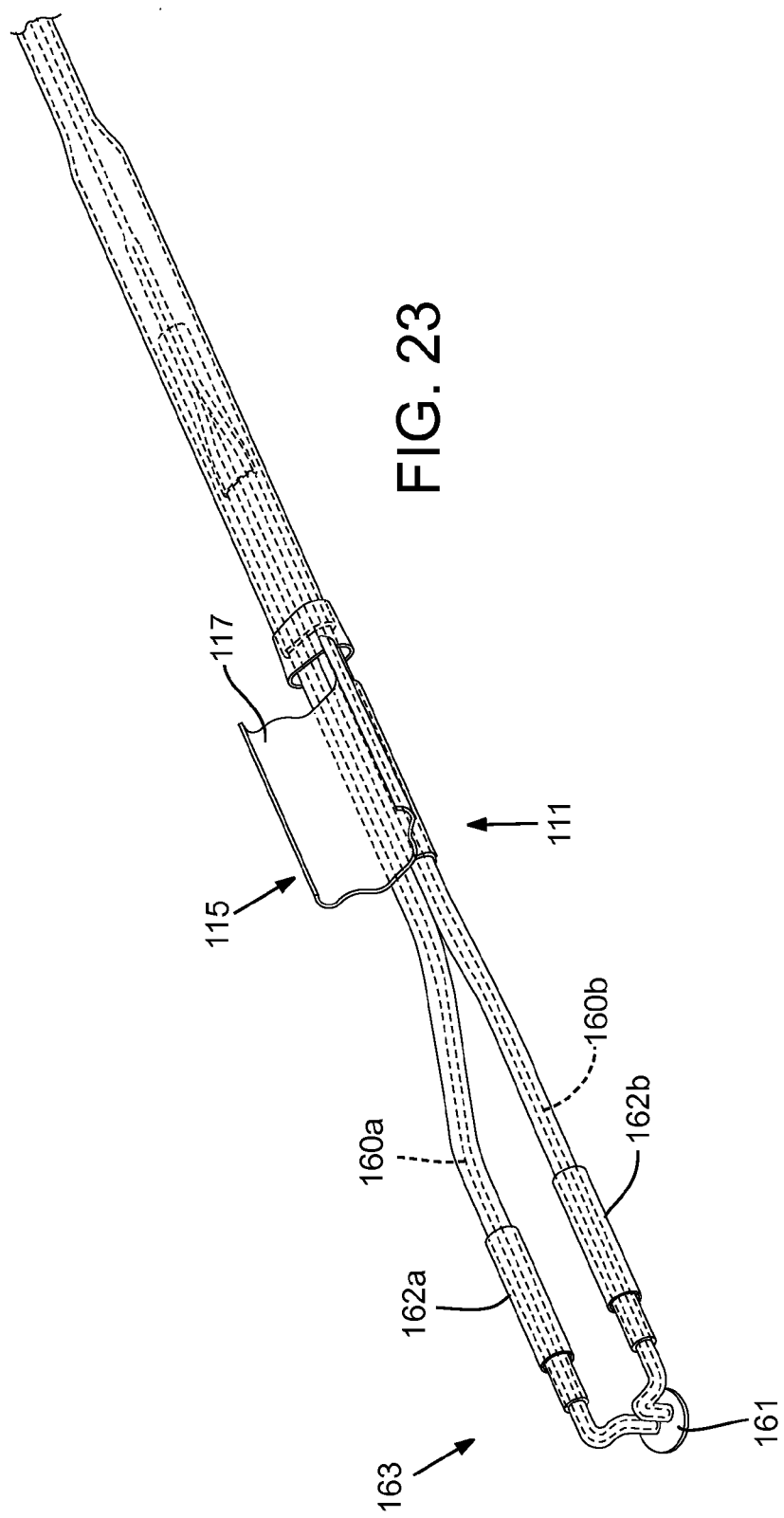

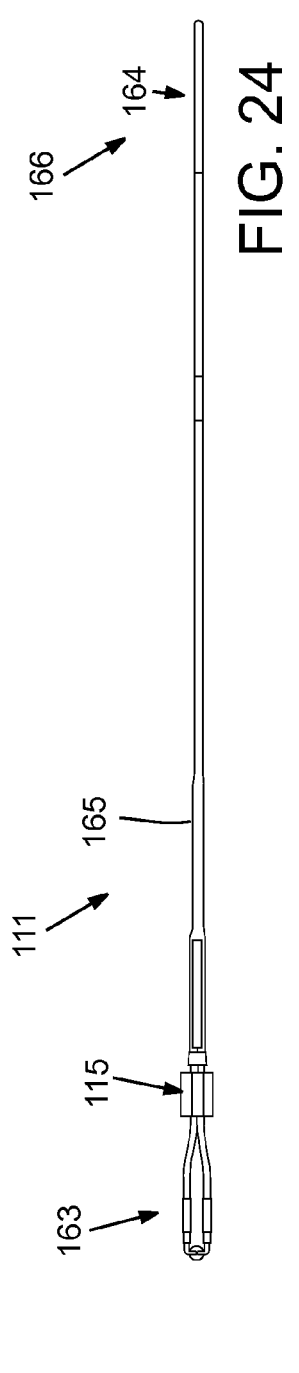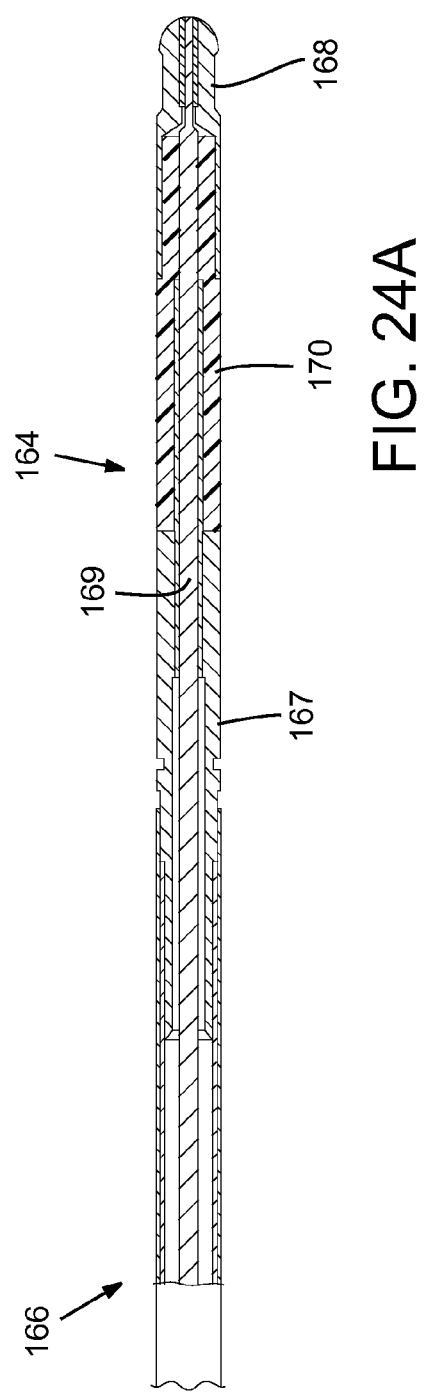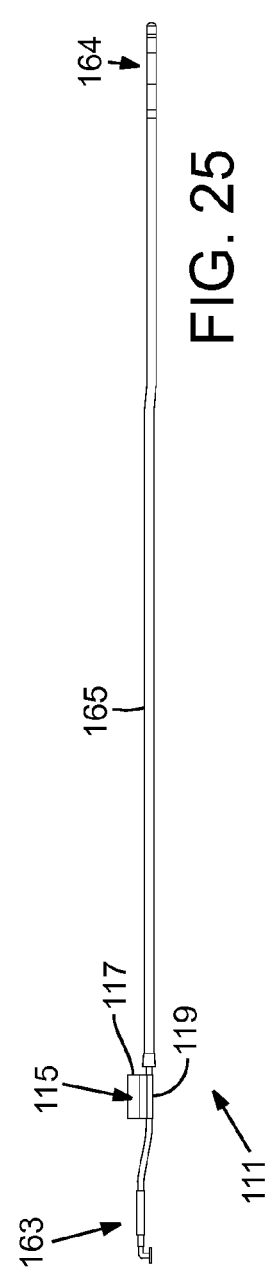

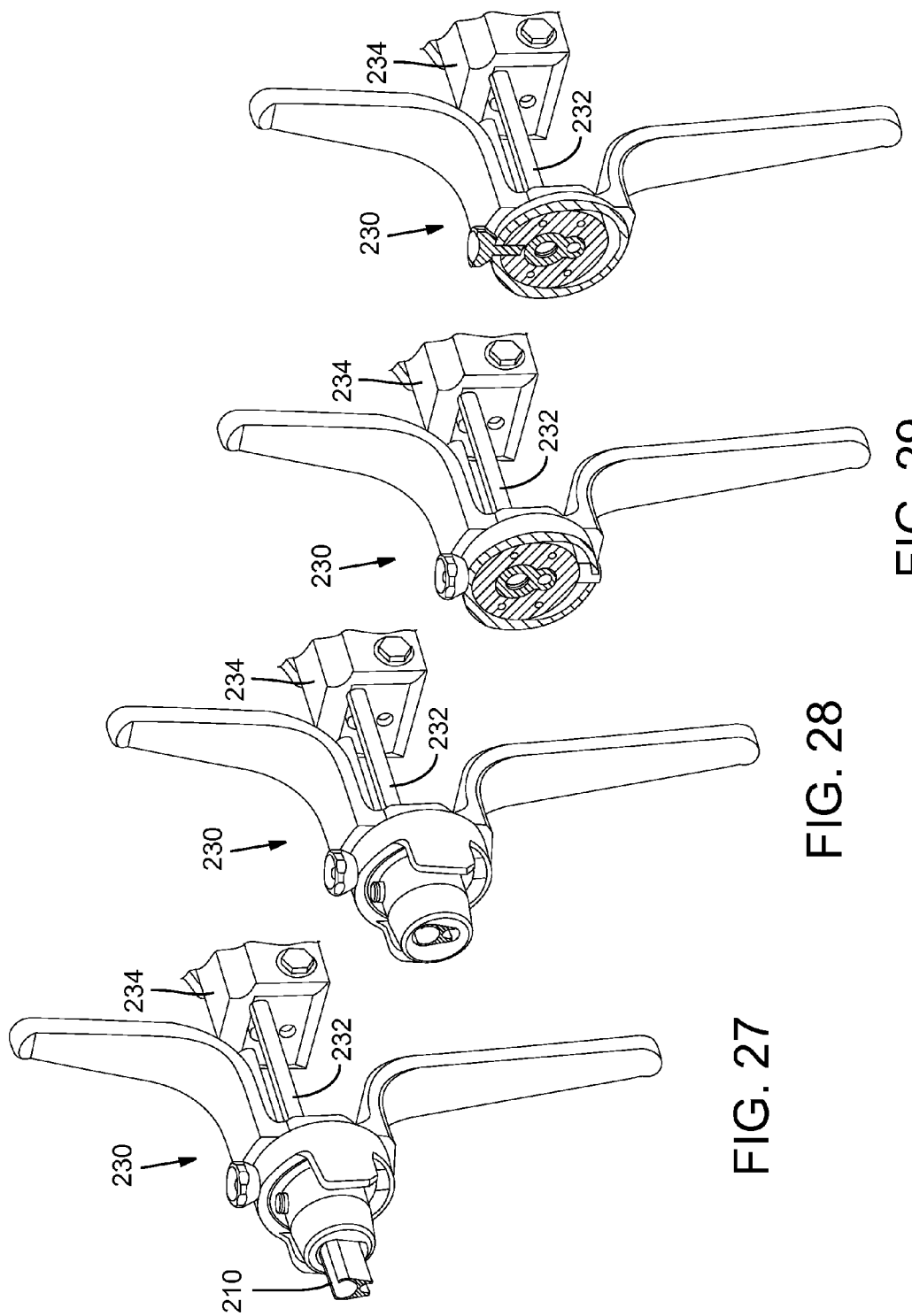

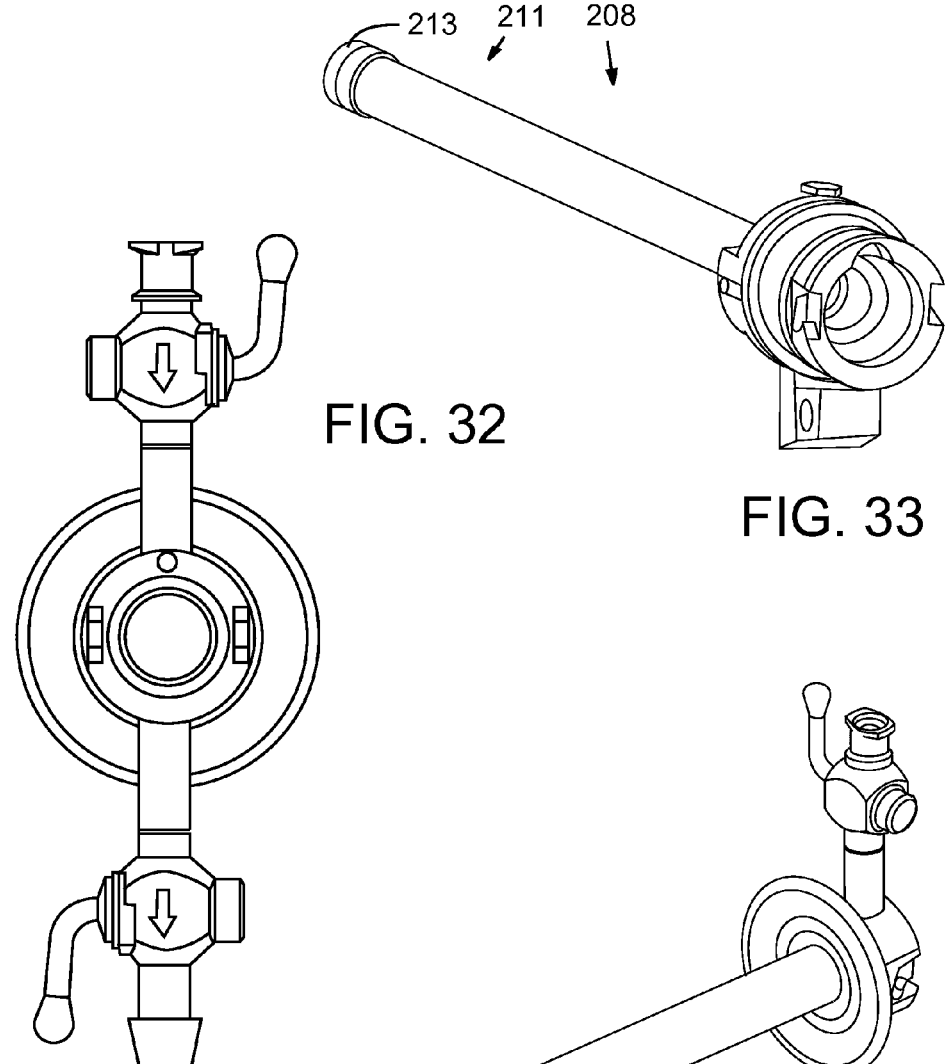
FIG. 32
FIG. 33
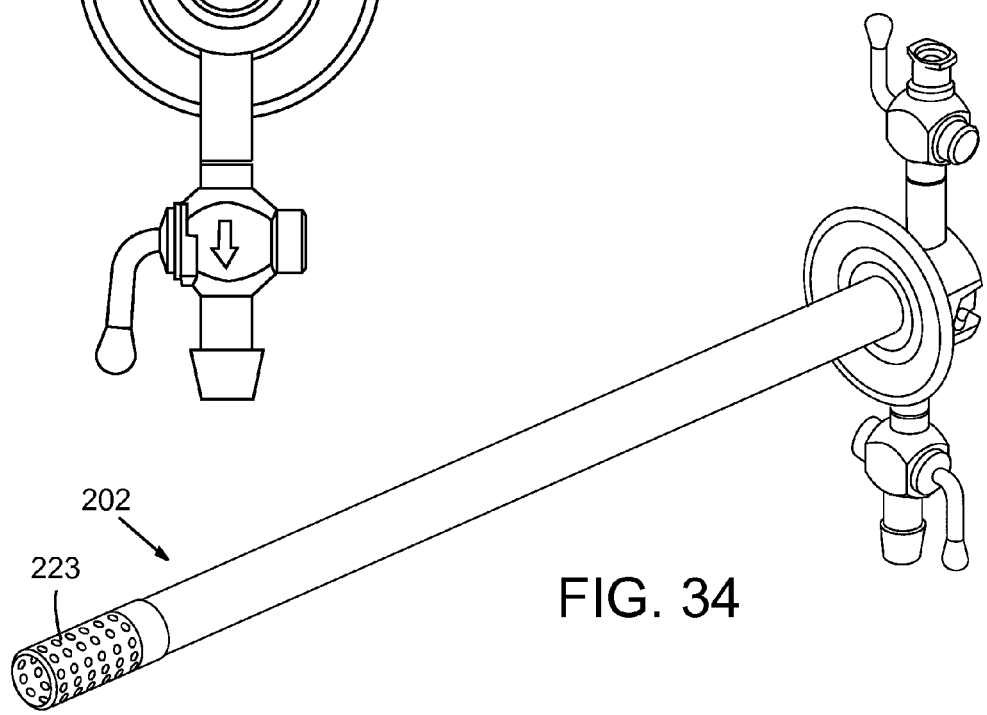
FIG. 34

CONTINUOUS FLOW ENDOSCOPE SYSTEMS

CROSS-REFERENCE TO RELATED APPLICATIONS

This application claims the benefit of and priority to U.S. Provisional Patent Application No. 61/349,805, filed May 28, 2010, the contents of which are hereby incorporated by reference in their entirety, as if recited in full herein, for all purposes.

BACKGROUND

This application, and the innovations and related subject matter disclosed herein, (collectively referred to as the "disclosure") generally concern medical instruments configured for viewing, treating or otherwise manipulating an anatomical target site in a human or animal body. Such instruments can be configured as, for example, medical endoscope instruments and/or related systems. Principles disclosed herein can be applied to a wide variety of medical instruments (e.g., resectoscopes, laparoscopes).

Conventional endoscopes have an elongate outer sheath configured for insertion into an anatomical region normally obscured from view, treatment or other manipulation. Such an anatomical region and tissue within and/or adjacent to such a region are collectively referred to herein as "target sites" and individually referred to as a "target site."

In some types of endoscopes, such as resectoscopes, the elongate outer sheath typically defines a distal end portion configured to house at least one device configured to view, treat and/or otherwise manipulate a target site. As used herein, "internal instrument" means a device configured to be slideably received in a sheath of an endoscope and to view, treat and/or otherwise manipulate a target site.

In many instances, an internal instrument can move longitudinally to and fro relative to the distal end portion, defining a working stroke through which the device can move. A length of an insertable portion of the elongate outer sheath, plus a length of the portion of the working stroke extending beyond the distal end of the outer sheath can define a maximum insertion length of an endoscope.

Some outer sheaths house two or more internal instruments. For example, U.S. Pat. No. 5,287,845, which is hereby incorporated by reference in its entirety, describes an endoscope for transurethral surgery having a main body non-rotatably supporting an optical system and a surgical instrument (e.g., scissors, tongs or, typically, a high-frequency cutting electrode). An outer tube affixed to the main body tubularly encloses the optical system and the surgical instrument. The outer tube of U.S. Pat. No. 5,287,845 is rotatably mounted relative to the main body, the optical system and the surgical instrument.

When using such a conventional endoscope, visibility of the target site (sometimes also referred to as an "operative field") can be obscured by a turbid fluid. For example, in a medical environment, blood or another bodily fluid can obscure visibility. To address such poor visibility, some endoscopes have been configured to continuously inject a working fluid into the target site in an attempt to dilute the turbid fluid and improve visibility. For example, U.S. Pat. No. 3,835,842, which hereby incorporated by reference in its entirety, discloses an endoscope configured to supply a continuous inflow of clear irrigating fluid to an operative field and to continuously drain turbid fluid from the operative field.

Conventional endoscopes that provide continuous irrigation suffer from several disadvantages. For example, some conventional endoscopes do not provide a rotational coupling between an external surface in contact with the patient and the device configured to view, treat and/or manipulate the treatment site. In these embodiments, multiple removals and insertions may be necessary to reorient the device. Other conventional endoscopes combine continuous irrigation with a rotatable outer surface, but at the expense of higher outer diameters, which might impart more trauma than a smaller outer diameter would. Previous attempts at shrinking outer dimensions of endoscopes have met with limited success since internal instruments have a finite size.

Some conventional endoscope sheaths are perforated and define a plurality of openings extending through a wall of the outer sheath and being disposed adjacent the distal end of the sheath. Such perforations can allow a turbid fluid to flow from the treatment site into a channel within the outer sheath. The fluid may then be withdrawn through the endoscope. Although such perforations can improve fluid flow from the treatment site, they might also abrade the patient's tissue, causing more trauma to the tissue than a similarly-sized, continuous outer surface without perforations.

Some previously proposed endoscopes have incorporated a separate and distinct ceramic tip component to thermally and/or electrically insulate a distal tip of an outer sheath, an inner sheath, or both. Insulating the inner or outer sheath from internal instruments (e.g., an electrode) reduces the likelihood of unintended portions of the instrument being subjected to electrical and/or thermal effects, which may damage the instruments and cause user/patient hazards.

Such tips have been attached to an outer sheath using an adhesive material, a mechanical fastener (e.g., a dimple on the tube's wall), or both. Ordinarily, a groove or other feature has been formed in the ceramic (e.g., by grinding) to accommodate such a mechanical fastener.

Improvements to conventional endoscopes have been difficult to achieve and various approaches have met with limited success, at least in part, because individual components (e.g., electrodes, telescopes) have been standardized and are widely available commercially. Accordingly, designers tend to use previously available components in an attempt to keep costs at reasonable levels, which in turn limits the extent of possible improvements.

In addition, there are many competing requirements that a designer must attempt to satisfy. For example, to reduce patient trauma, an outer diameter of an endoscope sheath is desirably as small as possible. Nonetheless, to obtain useful performance from internal instruments (e.g., well-resolved images from visualization instruments, such as, for example, an optical telescope) received within the outer sheath, an interior dimension is desirably as large as possible to provide sufficient maneuverability of internal instruments and/or sufficiently open channels for fluid inflow and outflow. In addition, larger internal dimensions can allow higher performance internal instruments to be used. Thus, improving performance in one area has typically resulted in little to no, and sometimes negative, performance gains in other areas. Despite the many configurations that have been proposed, a need remains for endoscopes that reduce the risk of patient trauma. For example, there is a need for endoscopes having a smaller outer diameter. A need also exists for endoscopes with longer working strokes. High-quality imaging devices for endoscopes are also needed. Endoscopes with improved inflow and outflow rates are also needed. In addition, a need exists for improved insulation between internal instruments and the distal tip of the endoscope. And, there remains the need for low-cost and economical endoscopes.

SUMMARY

The innovations disclosed herein overcome many problems in the prior art and address one or more of the aforementioned or other needs. In certain embodiments, the innovations disclosed herein are directed to endoscope instruments and/or related systems that include a hollow outer sheath configured for insertion into a patient's body.

A hollow inner sheath can be receivable within the outer sheath and may be configured to slideably receive a first internal instrument, such as, for example, an instrument configured to view, treat and/or manipulate a target site within the patient's body. The inner sheath can be rotatable within the outer sheath such that the inner sheath is configured to orbit within the bore of the outer sheath about the common axis of rotation.

A working element can be configured to rotatably support at least the first internal instrument and a second internal instrument such that at least the first internal instrument and the second internal instrument are rotatable about a common axis of rotation being substantially coextensive with a longitudinal axis of the outer sheath. The working element can have at least one guide rail extending longitudinally along the axis of rotation and an actuator block can be slideably mountable to the at least one guiderail and so securable to at least one of the instruments as to be able to urge the at least one of the internal instruments longitudinally along the outer sheath.

In some embodiments, a longitudinal axis of the at least one guide rail is spaced from the first internal instrument and the second internal instrument. In some embodiments, the at least one guide rail includes at least two guide rails positioned in a laterally flanking relationship relative to the first internal instrument. Some disclosed actuator blocks define at least one guide-rail bore. In such an embodiment, a guide rail can extend through the guide-rail bore.

Some disclosed working elements include a grommet configured to sealingly receive the first internal instrument and the second internal instrument in respective first and second bores. The first bore can define a first lip configured to urge against the first internal instrument, and the second bore can define a second lip configured to urge against the second internal instrument. The first lip can extend radially inwardly from an outer circumference of the first bore and the second lip can extend radially inwardly from an outer circumference of the second bore. The first lip and the second lip can be longitudinally spaced from each other along an insertion direction of the first and second internal instruments.

In certain embodiments, the working element further includes an adapter element and a rotatable element. The adapter element can define a longitudinally recessed region and a working fluid inlet bore. The rotatable element can be received in the recessed region of the adapter element and can define a circumferentially-extending recess such that a circumferentially extending channel is defined between the rotatable element and the adapter element. The rotatable element can define a transverse bore fluidicly coupled to the working fluid inlet bore and to the circumferentially extending channel. The rotatable element can also define an internal instrument bore coupled to the transverse bore. The internal instrument bore can be fluidicly coupled to a bore through the inner sheath, such that the working fluid inlet bore is fluidicly coupled to an interior of the hollow inner sheath.

The inner sheath can extend distally of the working element. The second internal instrument can be positionable between the inner sheath and the outer sheath. In some embodiments, the second internal instrument can be movably securable to the inner sheath by a clip configured to conforms to the outer profile of the inner sheath and slidingly engage the inner sheath. The inner sheath can be axially asymmetric and the clip can have a corresponding axially asymmetric contour positioned in sliding engagement with the inner sheath.

In some instances, the second internal instrument is or includes an electrode assembly being positionable between the inner sheath and the outer sheath. The outer sheath can define a distal portion comprising a ceramic coating, and a plane defined by the outlet opening might not be parallel to the longitudinal axis of the outer sheath. In some embodiments, a gap between a distal portion of the inner sheath and a distal portion of the outer sheath can define an outlet opening of a fluid conduit configured to convey fluid from the patient's body. The second internal instrument can include a distally positioned, energizable element being positionable within or adjacent to the outlet opening. The outer sheath can define a substantially cylindrically shaped outer surface free of any outlet openings of a fluid conduit configured to carry fluid away from a target site.

Other innovative endoscopes are disclosed. For example, some disclosed endoscopes have a hollow inner sheath configured to slideably receive a first internal instrument and a second internal instrument. Such an inner sheath can be receivable within the outer sheath. In such an endoscope, a working element can have at least one guide rail extending longitudinally along the outer sheath, an actuator block being slideably mountable to the guide rail and a grommet defining a first bore configured to receive the first internal instrument and a second bore configured to receive the second internal instrument. The actuator block can be securable to at least one of the internal instruments so as to be able to urge the at least one of the internal instruments longitudinally along the outer sheath as the actuator block slides along the at least one guide rail.

The first bore can define a first lip configured to mate with the first internal instrument and a second lip configured to mate with the second internal instrument. The first lip can extend radially inwardly from an outer circumference of the first bore and the second lip can extend radially inwardly from an outer circumference of the second bore. The first lip and the second lip can be longitudinally spaced from each other along an insertion direction of the first and second internal instruments.

Endoscopes according to the innovative subject matter can be configured as one or more of a resectoscope, a laproscope, a baroscope, a bronchoscope, a colonoscope, a gastroscope, a duodenoscope, a sigmoidoscope, a push enteroscope, a choledochoscope, a cystoscope, a hysteroscope, a laryngoscope, a rhinolaryngoscope, a thorascope, a ureteroscope, an arthroscope, a candela, a neuroscope, an otoscope, and a sinuscope.

The foregoing and other features and advantages will become more apparent from the following detailed description, which proceeds with reference to the accompanying drawings.

BRIEF DESCRIPTION OF THE DRAWINGS

The drawings briefly described below show embodiments of various aspects of the innovations disclosed herein, unless expressly identified as illustrating a feature from the prior art.

FIG. 2 is an isometric view from above the endoscope shown in FIG. 1 with the outer sheath partially cut away to reveal internal features.

FIG. 2A is an isometric view of the distal end portion of the endoscope shown in FIG. 2 with the outer sheath partially cutaway to reveal internal features.

FIG. 2B is a partially cutaway, isometric view of the distal end portion of the outer sheath showing the tip portion coated with a dielectric material.

FIG. 4 is an isometric view of the endoscope shown in FIG. 1 showing a cross-section taken along section 4-4 in FIG. 3, and showing the outer sheath partially cut away.

FIG. 5 is an isometric view of the endoscope shown in FIG. 1 showing a cross-section taken along section 5-5 in FIG. 3.

FIG. 6 is an isometric view of the endoscope shown in FIG. 1 showing a cross-section taken along section 6-6 in FIG. 3.

FIG. 7 is an isometric view of the endoscope shown in FIG. 1 showing a cross-section taken along Section 7-7 in FIG. 3.

FIG. 8 is an isometric view of the endoscope shown in FIG. 1 showing a cross-section taken along section 8-8 in FIG. 3.

FIG. 9 is an isometric view of the endoscope shown in FIG. 1 showing a cross-section taken along section 9-9 in FIG. 3.

FIG. 23 is an isometric view of an exemplary electrode.

FIG. 24 is a top plan view of the electrode shown in FIG. 23. FIG. 24A shows details of a portion of FIG. 24.

FIG. 25 is a side elevation view of the electrode shown in FIG. 23.

FIG. 27 shows a sectioned, isometric view of the proximal end of the instrument portion shown in FIG. 26 from above and to the left of the proximal end. A cross-section taken along section 26-26 in FIG. 26 is also shown.

FIG. 28 shows an isometric view of part of the proximal end of the instrument portion shown in FIG. 26 from above and to the left of the proximal end of the instrument portion. A cross-section taken along section 27-27 in FIG. 26 is also shown in FIG. 28.

FIG. 29 shows an isometric view of part of the proximal end of the instrument portion shown in FIG. 26 from above and to the left of the proximal end of the instrument portion. A cross-section taken along section 28-28 in FIG. 26 is also shown.

FIG. 30 shows an isometric view of part of the proximal end of the instrument portion shown in FIG. 26 from above and to the left of the proximal end of the instrument portion. A cross-section taken along section 29-29 in FIG. 26 is also shown.

FIG. 32 shows an isometric view of the inner sheath shown in FIG. 31 from a position behind and above the proximal end of the inner sheath.

FIG. 33 shows an end-elevation view of the outer sheath shown in FIG. 31.

FIG. 34 shows an isometric view of the outer sheath shown in FIG. 31 from a position above and the left of the distal end of the outer sheath.

DETAILED DESCRIPTION

The following describes various principles related to instruments configured for viewing, treating and/or manipulating regions normally obscured from view by way of reference to exemplary instruments, such as, for example, endoscopes. One or more of the disclosed principles can be incorporated in various instrument configurations to achieve any of various characteristics. Instruments described in relation to particular applications, or uses, are merely examples of instruments incorporating the innovative principles disclosed herein and are used to illustrate one or more aspects of the various innovative principles. Accordingly, instruments with configurations different from those shown in the accompanying drawings can embody such innovative principles or can be used in applications not described herein in detail, such as, for example, in specialized cameras (e.g., in industrial and medical endoscopes, telescopes, microscopes, and the like), as well as in general commercial and professional video and still cameras. Accordingly, such alternative embodiments also fall within the scope of this disclosure.

Overview

Figure 1:
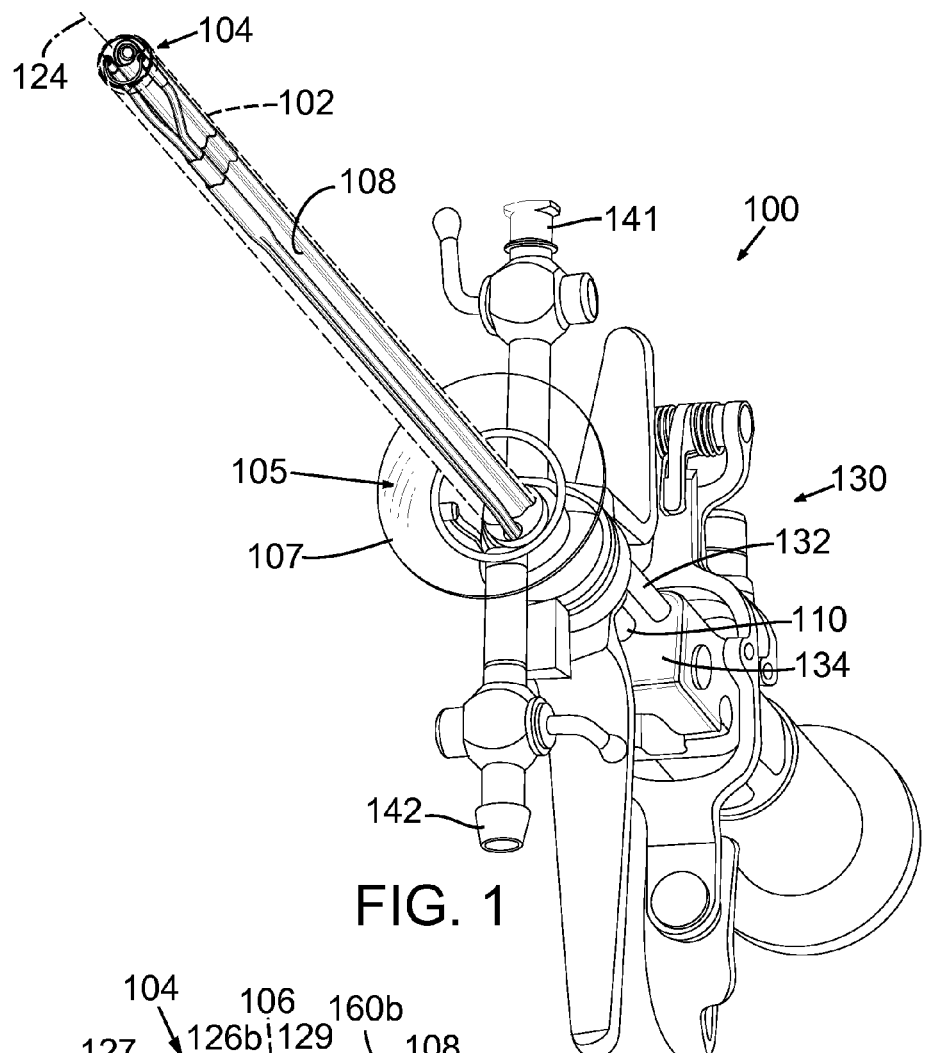
FIG. 1 is an isometric view from below a first exemplary embodiment of an instrument configured for viewing areas of a patient's body normally obscured from view. The instrument shown in FIG. 1 is configured as an endoscope (e.g., a resectoscope).
Figure 1A:
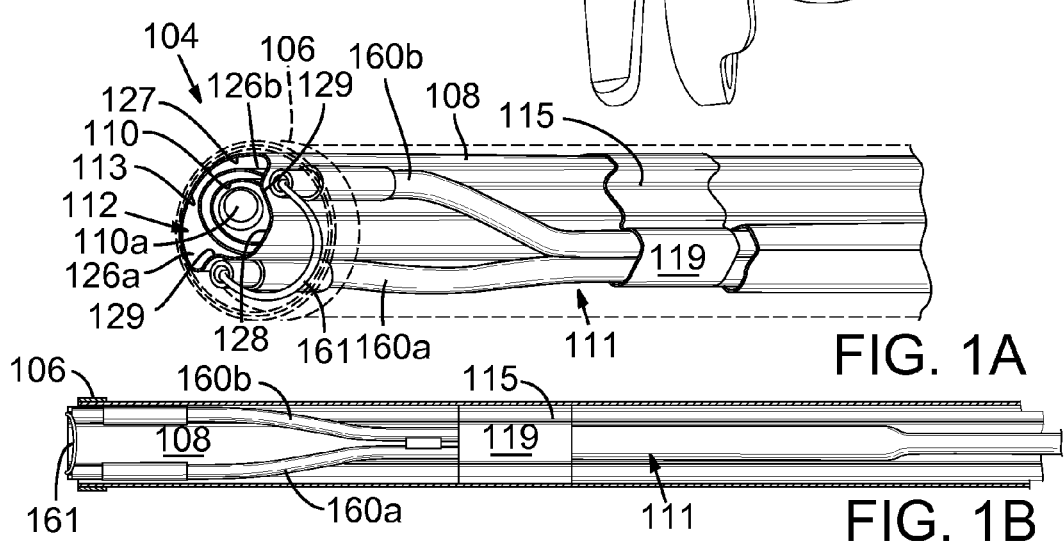
FIG. 1A is an isometric view of a distal end portion of the endoscope shown in FIG. 1 with the outer sheath removed (dashed lines) to reveal internal features.
Figure 1B:
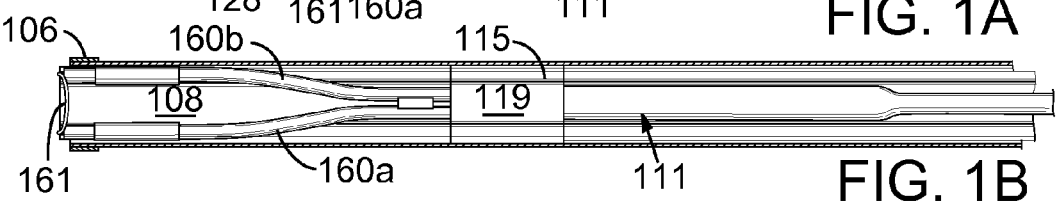
FIG. 1B is a bottom plan view of the distal end portion shown in FIG. 1A with the outer sheath partially cut away to reveal internal features.

As shown in FIG. 1, an instrument 100, such as for example, an endoscope, can have a hollow outer sheath 102 configured for insertion into a patient's body, such as through a body lumen and/or through an incision (not shown). A hollow inner sheath 108 can be positioned within the outer sheath 102, and can slideably receive one or more internal instruments. In some instances, a distal portion 104 of the outer sheath 102, a distal portion of the inner sheath 108, or both, can be coated with a dielectric material 106, such as, for example, a ceramic (FIGS. 1A and 1B). In other embodiments, as is the case with prior art embodiments, a dielectric tip can be implemented into the distal portion of the outer sheath 102, a distal portion of the inner sheath 108, or both.

Such a dielectric coating tends to insulate the respective, e.g., outer, sheath from an energizeable element 161, keeping the respective sheath from being in an active electrical circuit, or path, or plasma zone. Insulating the outer sheath 102 from the energizeable element 161 reduces the likelihood of a user and/or the patient being electrically shocked, since the outer sheath is often electrically coupled to a portion of the endoscope grasped by the user and is in direct contact with the patient.

The dielectric coating can be a thin coating (e.g., about 0.020 inch thick) having sufficient dielectric properties to insulate the underlying component, from coming into electrical contact with an energizeable element 161. A thin coating allows the endoscope to have a small outer dimension as compared to a thick coating. Also, a dielectric coating can be much thinner than a separate and distinct tip of the prior art, at least in part because the coating can be supported by the underlying component. In addition, the substrate is less prone to manufacturing defects that can lead to cracking during use, potentially reducing manufacturing costs, repair costs, or both. The metal substrate would enhance the mechanical strength of the dielectric insulation, and, in case of the ceramic coating is damaged during the surgical procedure, would keep the brittle ceramic from falling apart.

In some embodiments, an entire outer surface of the insertable portion of the outer sheath is coated. Such a full-length coating can improve patient comfort, as compared to a partially coated outer sheath, or a prior art outer sheath.

The inner sheath 108 can have a hollow body capable of conveying a working fluid (e.g., a generally clear irrigation fluid, such as, for example, saline) and/or slideably receiving a device configured to view, treat and/or manipulate a target site. As shown in FIG. 1, such a device can extend longitudinally along the hollow interior, obstructing a portion of the cross-section of the hollow interior along its length. In FIG. 1, the internal instrument is a telescope 110 that includes an objective lens at the distal end and an optical train leading to a viewing lens at the proximal end. The telescope may also be in the nature of an electronic imaging device that includes a pixellated image sensor, such as a CCD or CMOS sensor at a distal end, and supporting electronics.

Some instruments 100, including the one shown in FIG. 1, are configured to continuously and/or intermittently introduce a working fluid from the fluid conduit 112 defined by the inner sheath 108 to a target site. For example, the inner sheath 108 can define a fluid supply opening 113 positioned at its distal end through which opening the working fluid can exhaust from the inner sheath to provide an inflow 114 (FIG. 2A) of working fluid to a target site.

As used herein, "inflow" means a net flow of material (e.g., a fluid, such as a working fluid, with saline being but one example) into a defined region (e.g., a target site, or a body cavity surrounding a target site). Accordingly, an opening defined by an instrument through which a net flow of a fluid can pass from the instrument into such a defined region is sometimes referred to in the art as an "inflow opening."

In contrast, as used herein, "outflow" means a net flow of material (e.g., a fluid, such as, for example, a mixture of a turbid fluid and a generally clear working fluid) out of, or from, a defined region (e.g., a target site, or a body cavity surrounding a target site) into, for example, an instrument. Accordingly, an opening defined by an instrument through which a net flow of a fluid can pass out of, or from, such a defined region into, for example, a conduit defined by the instrument is sometimes referred to in the art as an "outflow opening."

Referring to FIG. 2A, an outer surface 116 of the inner sheath 108 can be inwardly spaced from an opposing inner surface 118 of the outer sheath 102 to define a gap 120 (FIG. 3A) between the opposing walls of the inner sheath and the outer sheath. The gap 120 can extend around at least a portion of a perimeter of the outer surface 116 of the inner sheath 108, and can extend longitudinally along the inner sheath 108 and the outer sheath 102 so as to define a fluid conduit 122 between the inner sheath and the outer sheath extending longitudinally along the inner and the outer sheaths. As shown, for example, in FIGS. 1A, 2A and 3A, the gap 120 can extend sufficiently longitudinally of the sheaths 102, 108 to define an opening 123 at a distal end of the endoscope.

Some instruments 100 are configured to continuously drain a fluid (e.g., a mixture of a turbid fluid and an injected working fluid, such as, for example, a mixture of blood and saline) from a target site. For example, the gap 120 defined between the inner and outer sheaths 102, 108 can convey a fluid from the opening 123 in the distal end 104 to an outlet port 142 (FIG. 1) fluidically coupled to, for example, a low-pressure drainage system (not shown). In such a configuration, the opening 123 can be considered an outflow opening.

As shown in FIGS. 1A and 2A, such an outflow opening 123 can be oriented generally perpendicularly to an axial direction of the outer sheath. That is to say, a unit vector normal to a plane (not shown) defined by the outlet opening 123 can be oriented substantially parallel to a longitudinal central axis 124 of the outer sheath 102. The energizeable element 161 is positionable within or adjacent to the outlet opening 123 so that the energizeable element 161 can face the outlet opening 123. Nonetheless, other outflow openings (not shown) can be oriented at an oblique angle relative to the longitudinal central axis 124 of the outer sheath 102, and still other outflow openings can be oriented such that a normal vector is oriented perpendicularly relative to the longitudinal central axis 124 of the outer sheath, such as with the perforations 223, shown in FIG. 31.

In addition to the innovative sheath features briefly described above, the instrument 100 also incorporates innovative features of a working element 130. The working element 130 shown in FIG. 2 is configured to (1) rotatably couple the outer sheath 102 to each device configured to view, treat and/or otherwise manipulate a target site; (2) fluidicly couple the distally positioned inflow opening 113 defined by the inner sheath 108 to a fluid supply (not shown); (3) fluidically couple the distally positioned outflow opening 123 defined between the inner sheath 108 and the outer sheath 102 to a fluid drain (not shown); and (4) provide a working stroke length of up to 1.025 inches.

Combination of the inner sheath into the working element increases the insertion length over conventional insertion lengths. Such an increase could be as much as 0.25 inches, which is considered a substantial improvement in insertion length. Such improved working stroke lengths provide users with more flexibility in maneuvering an internal instrument and can reduce the need to reposition the outer sheath 102 to reach a portion of a target site previously beyond the reach of an internal instrument. A typical maximum insertion length for the outer sheath can measure between about 7.0 inches and about 8.0 inches, such as, for example, between about 7.5 inches and about 7.8 inches.

As will be described more fully below, the illustrated working element 130 is configured to rotatably support at least a first internal instrument, such as a telescope 110, and a second internal instrument, such as an electrode 111, such that the at least first and second internal instruments are rotatable about a common axis of rotation. For the endoscope 100, the common axis of rotation is substantially coextensive with the longitudinal central axis 124 (FIG. 1) of the outer sheath 102. The first internal instrument 110 and the second internal instrument 111 orbit about the longitudinal central axis 124 on opposite side of the longitudinal central axis 124. The inner sheath 108 orbits about the longitudinal central axis 124 with the first internal instrument 110 and the second internal instrument 111.

One or more guide rails 132 can extend along the axis of rotation, and an actuator block 134 can be slideably mounted to the guide rails 132. The first and the second internal instruments 110, 111 can be sufficiently secured to the actuator block 134 such that the actuator block 134 urges the internal instruments 110, 111 longitudinally along the outer sheath 102 as the actuator block slides along the guiderails 132.

In addition, the working element 130, outer sheath 102 and inner sheath 108 can be so cooperatively configured as not to leak as the internal instruments 110, 111 slide longitudinally of the sheaths, or as the internal instruments (among other components) rotate relative to the outer sheath. Stated differently, the configurations of each of the working element 130, outer sheath 102 and inner sheath 108 can be so cooperatively configured as to substantially prevent leaks between rotationally engaged and/or slideably engaged surfaces. For example, a part of a rotatable element 150 of the working element 130 is configured to rotate within a sheath adapter 140 (FIGS. 11 through 21). Also, a rotatable element 150 can be configured to sealingly receive a grommet 151 (FIG. 22) through which at least a first internal instrument 110 and a second internal instrument 111 can extend in a sliding, sealed engagement.

Outer Sheath

An endoscope 100 can have an outer sheath 102 configured for insertion into, for example, a body lumen. The proximal end 105 of the outer sheath 102 can be rotatably coupled to a working element 130, as described more fully below.

An insertion limiter 107 can be positioned near the proximal end 105 of the outer sheath 102. By way of example, the insertion limiter 107 can have a disc member extending radially of and affixed to an outer surface of the outer sheath 102. In many instances, the outer sheath 102 can be inserted through a relatively small opening in a larger boundary (not shown) (e.g., the outer sheath can be inserted through an incision in a patient's skin, or through a urethral opening). The insertion limiter 107, having a larger radial dimension than the outer sheath 102, can urge against the boundary through which the outer sheath has been inserted, thereby limiting the depth to which the outer sheath can be inserted. The depth to which a component can be inserted is sometimes referred to as an "insertion depth." The length of an insertable portion of a component is sometimes referred to as an "insertion length."

The outer sheath 102 defines an open interior configured to receive one or more other components, as described more fully below. In some instances, as shown in FIGS. 1 and 2, the outer sheath 102 has a body defined by a hollow cylinder, or tube.

In certain embodiments, a distal portion 104 of the outer sheath 102 can be electrically and/or thermally insulated from one or more internal components, such as an internal instrument 110, 111. For example, the distal portion 104 can be internally and/or externally coated with a dielectric material 106, such as ceramic coating or a durable polymer coating or a ceramic material. Flouropolymers are but one example of a class of suitable polymers. Any dielectric material capable of producing a thin (e.g., about 0.015 inch to about 0.025 inch), insulative coating can be used. For example, an alumina coating, a flouropolymer coating or other coating capable of withstanding exposure to a plasma (e.g., having an average temperature of about 500-degrees Fahrenheit, or possibly higher). In other instances, the body of the outer sheath 102 can be formed entirely or partially of a dielectric material, such as a reinforced glass fiber or a plastic (e.g., a glass-epoxy tube with a Teflon coating).

Samples of ceramically coated stainless-steel tubes have been manufactured using a thermal spray technique. In such a technique, a cloud of alumina (or other suitable material) is blown through a torch or other heat source before coming into contact with a portion of a substrate, e.g., a portion of an outer sheath. Such a deposition process can deposit a thin (e.g., about 0.050 inch, or less) layer of, for example, alumina on the substrate. Subsequent layers can be added to form a generally unitary coating having a desired thickness, such as between about 0.015 inch and about 0.030 inch, with about 0.020 inch being an example. To promote bonding of a deposited ceramic layer to the substrate before the substrate has a previously built-up coating, the alumina cloud can be supplemented with a binder, such as a glass or metal powder. In some instances, the alumina powder forming the cloud include particles having an average particle size of about 1 micron.

Figure 3:
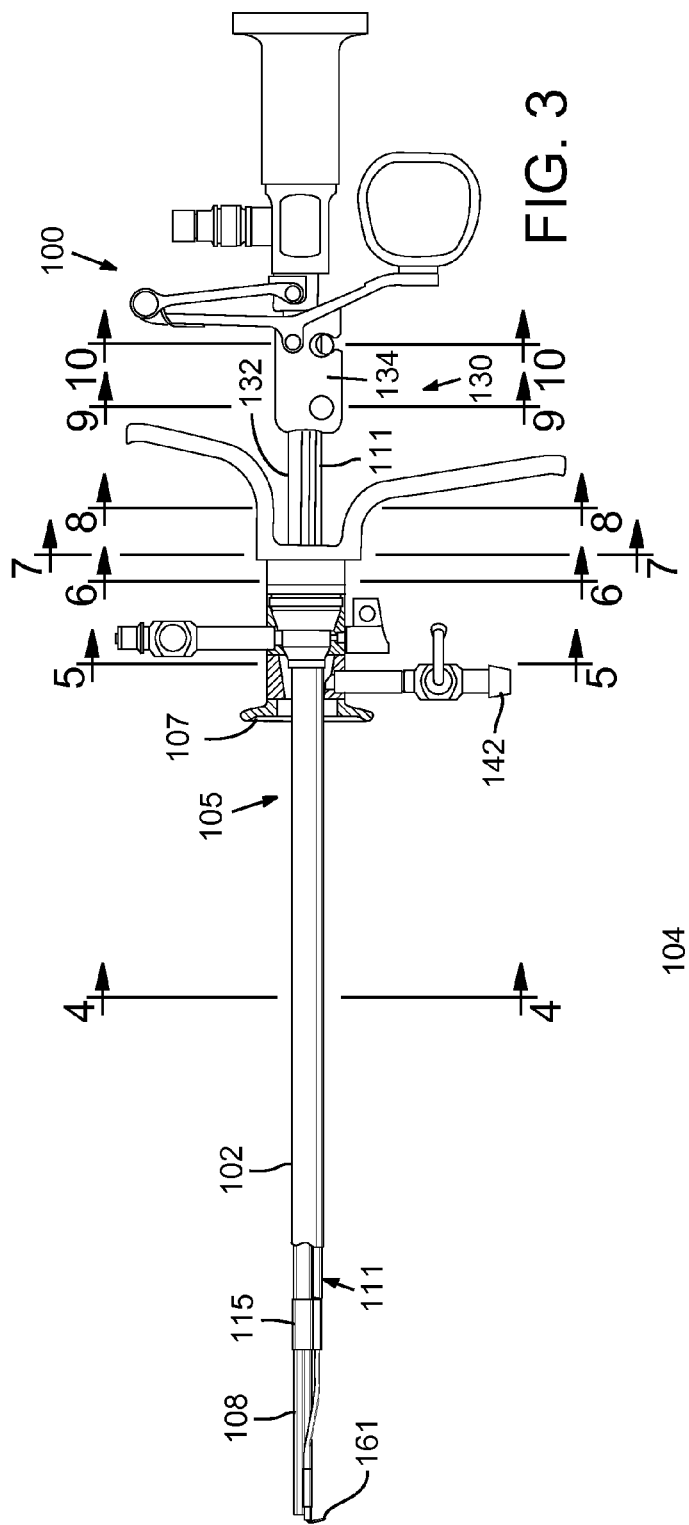
FIG. 3 is a side-elevation view of the endoscope shown in FIG. 1 with the outer sheath partially cut away to reveal internal features of the distal end portion of the endoscope.
Figure 3A:
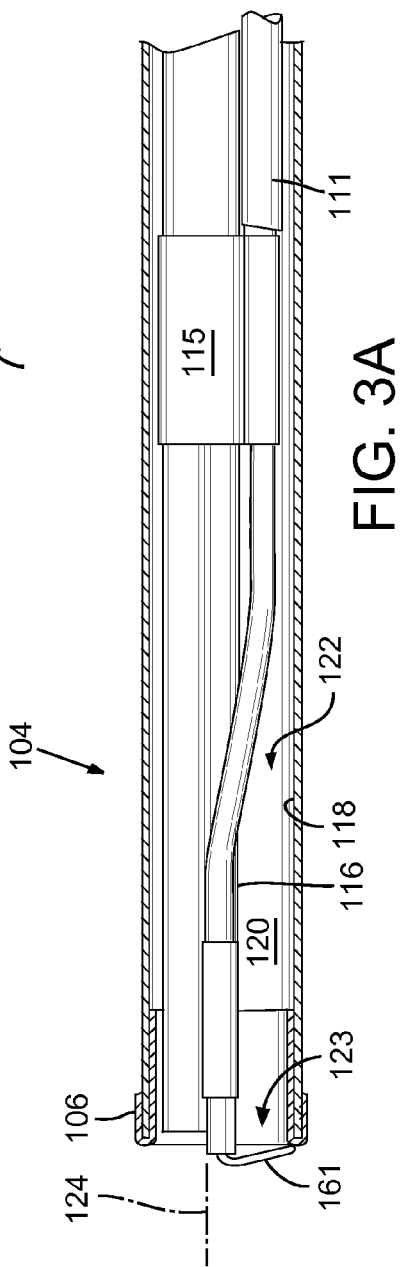
FIG. 3A is a magnified side-elevation view of part of the distal end portion shown in FIG. 3.
Figure 10:
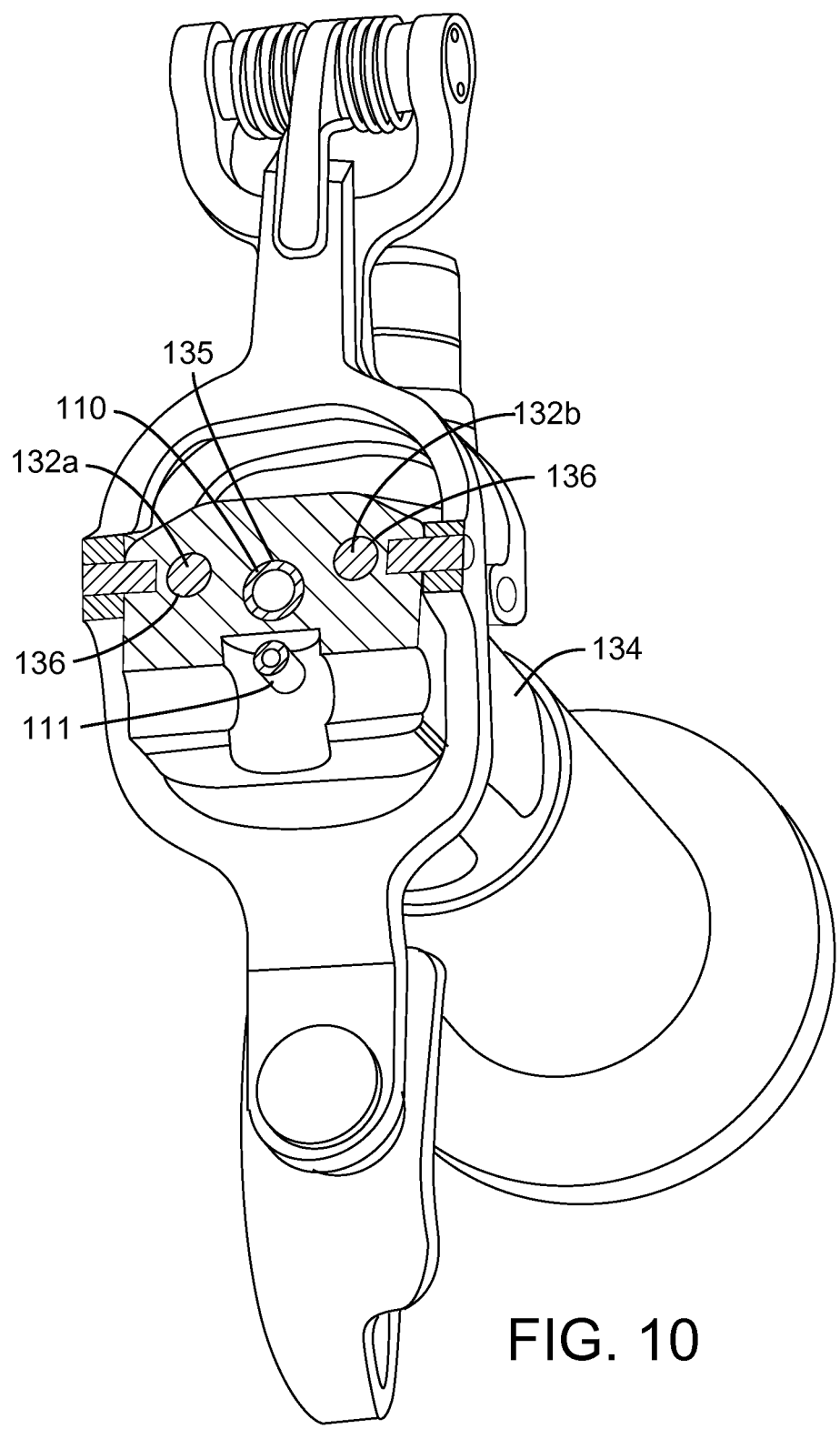
FIG. 10 is an isometric view of the proximal end of the endoscope shown in FIG. 1 showing a cross-section taken along section 10-10 in FIG. 3.

The outer surface 109 of the outer sheath 102 can be substantially continuous between its distal end 104 and the insertion limiter 107. Such a continuous outer surface 109 can reduce patient trauma during insertion and extraction of the outer sheath 102, as compared to a perforated outer surface. Nonetheless, the body of the outer sheath 102 can define one or more openings 223 (FIG. 31), or perforations, configured to fluidicly couple a region outside of the outer sheath to a region within the outer sheath such as the channel 122 (FIG. 3A).

In other embodiments, as is the case with prior arts, a dielectric tip can be implemented into the distal portion of the outer sheath 102.

Inner Sheath

Some inner sheaths 108 as disclosed herein can be slideably received within and rotatably coupled to an outer sheath 102. Such inner sheaths 108 can define a hollow body 108a (FIG. 35) and can slideably receive at least one internal instrument (e.g., a telescope 110 and/or an electrode 111) within the hollow body to allow the internal instrument to move longitudinally to and fro between a retracted proximal position (shown in FIG. 1) and a fully extended distal position (not shown). In the illustrated endoscope 100, the inner sheath 108 slideably houses a telescope 110 and defines unobstructed flow regions 126a, 126b configured to convey a fluid (e.g., a working fluid, such as, for example, saline). Stated differently, the inner sheath 108 has an internal cross-sectional profile configured to receive an internal instrument 110 and to leave at least one region 126a, 126b sufficiently unobstructed by the instrument to allow a sufficient flow rate of working fluid to by-pass the internal instrument.

Figure 35:
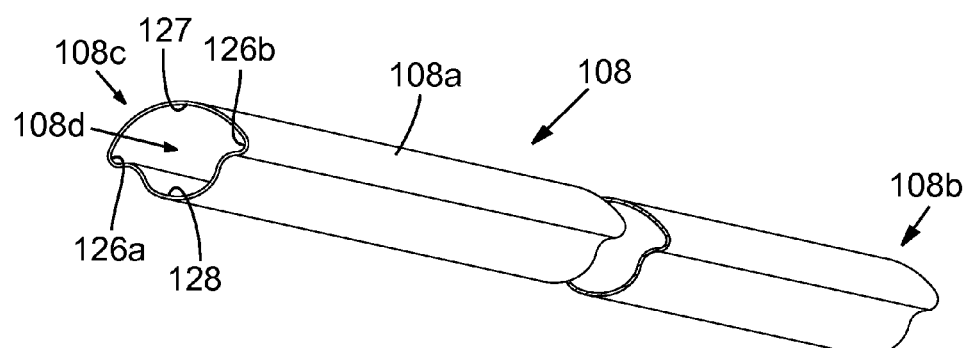
FIG. 35 shows an isometric view of an exemplary inner sheath.

The illustrated inner sheath 108 is an axially asymmetric tubular structure with a mushroom-shaped cross-section extending from the proximal end 108b of the inner sheath 108 to its distal end 108c, as illustrated in FIG. 35. In other words, the inner sheath defines an open central region having a concave upper boundary 127 and a concave lower boundary 128 (relative to the central region 108d), and opposed lobe regions 126a, 126b extending outwardly of the central region. A radius of curvature of the upper boundary 127 can be greater than a radius of curvature of the lower boundary 128, and a respective convex region 129 can at least partially extend between the upper and lower boundaries, thereby defining the opposed lobe regions 126a, 126b.

Figure 36:
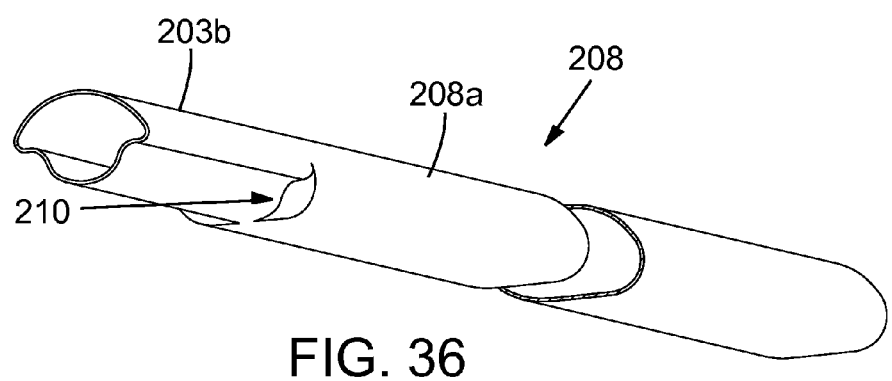
FIG. 36 shows an isometric view of an exemplary inner sheath.

Other embodiments of innovative inner sheaths are also possible. For example, the inner sheath 208 illustrated in FIG. 36 defines a body portion 208a having a generally oblong cross-sectional profile and a distally positioned, mushroom-shaped portion 203b extending from a distal end of the body portion. Although the transition region 210 is shown as being a generally abrupt transition, other inner sheath embodiments provide a generally smooth transition region between the body portion 208a and the distal portion 208b. (In FIGS. 35 and 36, the respective inner sheaths are shown having a broken section between the respective proximal and distal ends as a convention to indicate that each inner sheath can have any of a variety of lengths.)

An internal instrument 110 can be positioned within the open central region as shown in FIG. 1. The opposed lobe regions 126a, 126b can provide unobstructed conduits that allow a working fluid to by-pass the internal instrument obstructing the central region. The unobstructed flow regions can open at a distal end of the inner sheath, defining an inflow opening 113 surrounding the internal instrument (e.g., a telescope). The generally constant cross-sectional profile can provide a smooth flow of working fluid through the conduits 126a, 126b, reducing the likelihood of flow separation and/or other flow inefficiencies that might contribute to an increased loss of pressure head along a flow length. In addition, this configuration can provide one or more inflow, streams or jets, 114 of working fluid entering a target site near the distal end of the internal instrument 110. Such inflow, streams or jets, 114 can promote mixing of the working fluid and a turbid fluid present at the target site, increasing the rate at which the turbid fluid can be diluted and decreasing the time before visibility can be restored. In addition, such jets can manipulate or move portions of a target site, such as tissue, from obstructing an internal instrument. Such jets can also provide a high rate of cooling to a portion of the target site, as by impingement cooling.

In addition to providing unobstructed by-pass conduits 126a, 126b, the axially asymmetric cross-section of the inner sheath 108 provides a convenient contour for supporting an internal component 111 (FIGS. 22 through 24) in a mating engagement with an external surface of the inner sheath. For example, a clip 115 (FIG. 23) or other retention component can define an inner-sheath engagement portion 117 having a contour corresponding to the outer contour of the inner sheath 108 and configured to matingly engage the outer contour.

Figure 22:
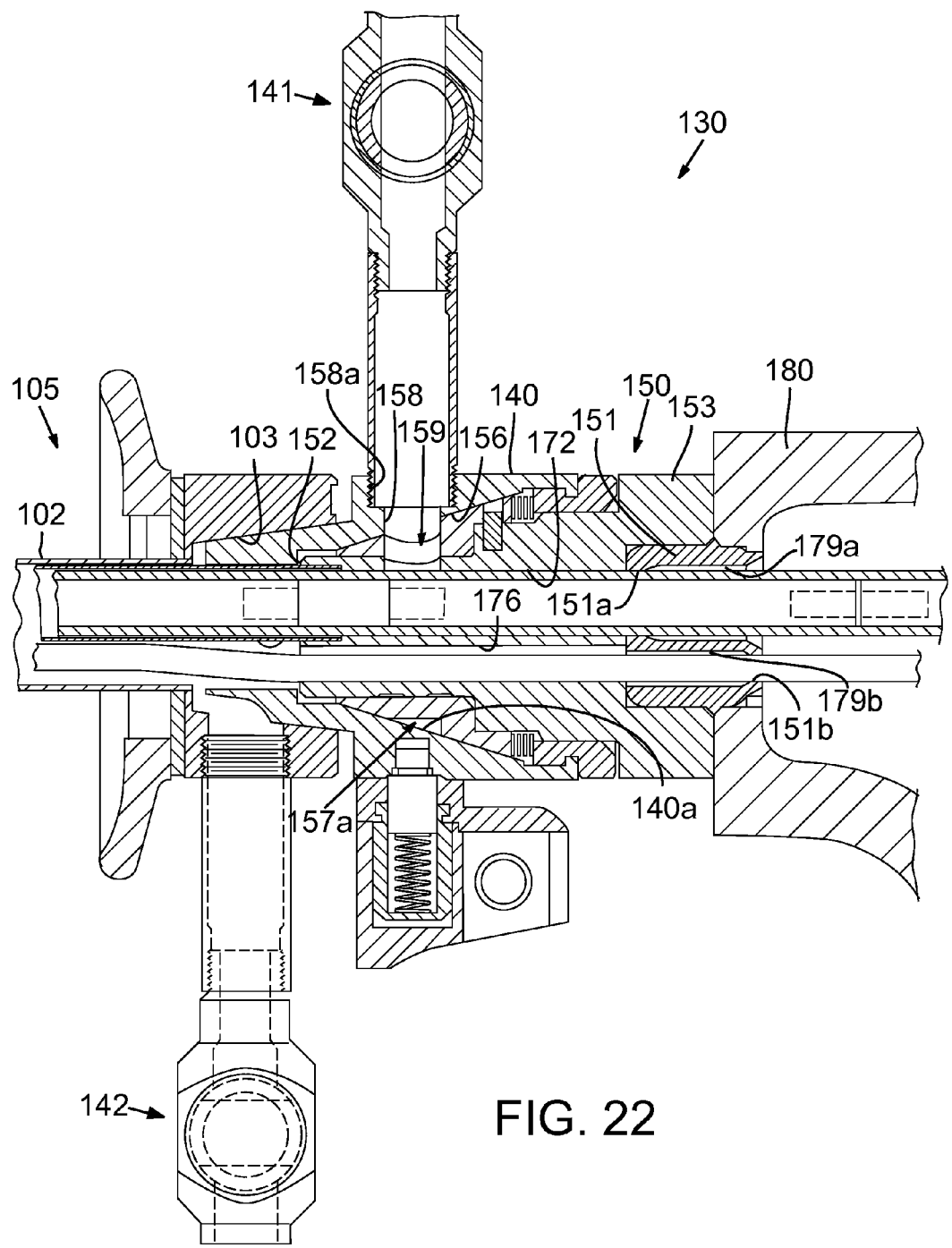
FIG. 22 is a part of a cross-sectional view of the working element of the endoscope shown in, for example, FIGS. 2 and 3.

As shown in FIGS. 22 through 24, an electrode assembly 111 can have first and second wire portions 160a, 160b extending longitudinally along the inner sheath 108. Each of the wire portions 160a, 160b can be positioned between the inner sheath 108 and the outer sheath 102 and adjacent a respective one of the opposed lobe regions 126a, 126b. An energizable element 161 is operatively coupled to the first and second wire portions 160a, 160b and positioned adjacent the lower boundary 128 of the inner sheath 108 between the walls of the inner and the outer sheaths 102, 108. When assembled in an endoscope 100, the inner sheath 108 can be positioned off-center relative to the outer sheath 102. A longitudinal axis passing through a centroid of the inner sheath cross-sectional area can be parallel to, but offset from, a longitudinal central axis 124 passing through a centroid of the outer sheath cross-sectional area.

Figure 31:
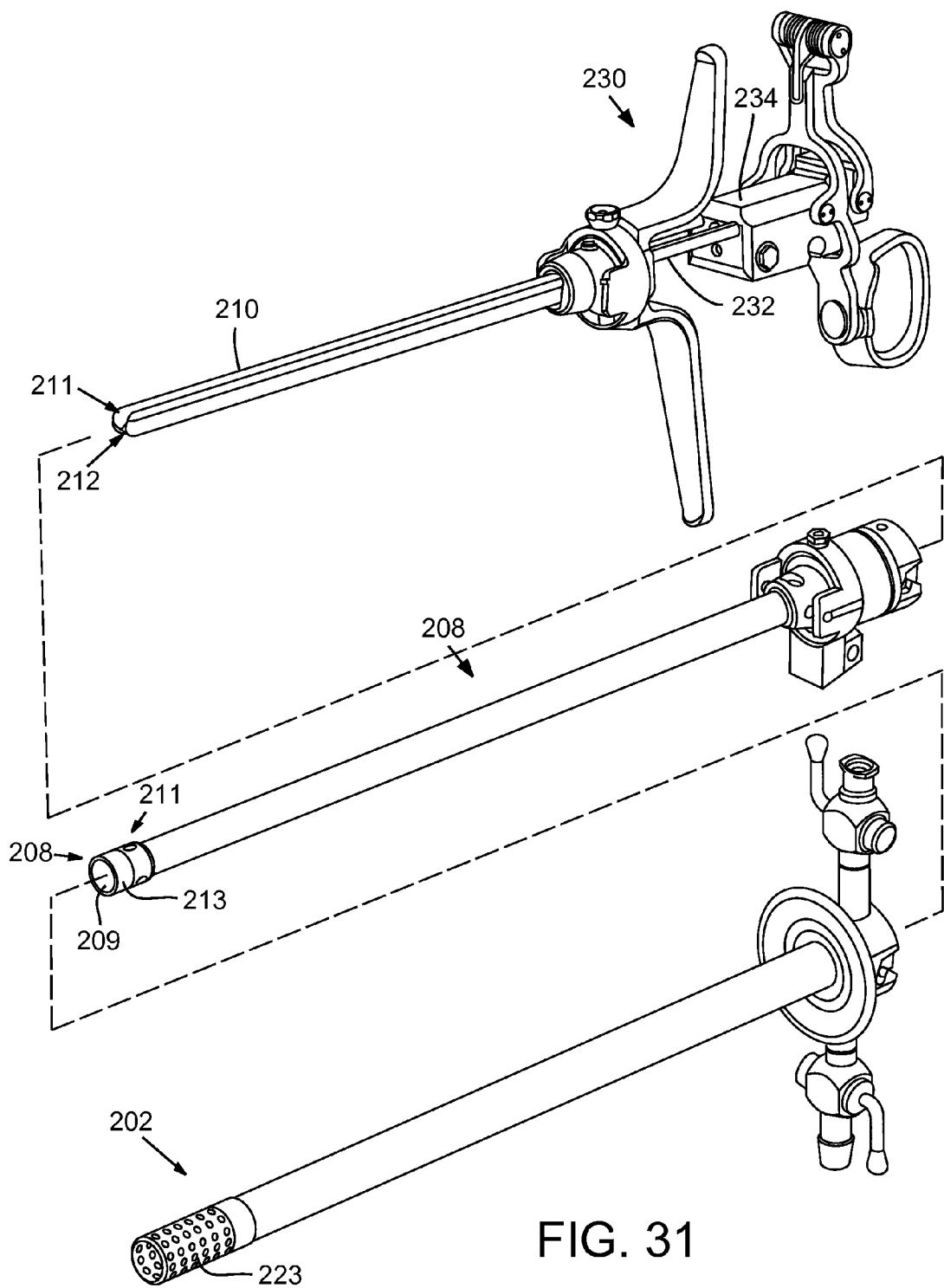
FIG. 31 is an isometric, exploded view of the instrument shown in FIG. 26, together with an inner and an outer sheath.

In other embodiments (e.g., as shown in FIG. 31), an inner sheath 208 can have a circular cross-sectional profile, and can be positioned concentrically within an outer sheath 202. Such alternative configurations are described more fully below.

Internal Instruments

As noted above, devices configured to be slideably received in an endoscope 100 and to view, treat and/or otherwise manipulate a target site are referred to herein as internal instruments. Such an internal instrument can be configured as an elongate telescope 110. As shown in FIG. 2, a telescope 110 can have an objective lens or other light-collecting component 110a positioned at a distal end of the telescope. Light (or an electrical or other signal carrying image information) can be conveyed from the distal end of the telescope 110 to its proximal end and/or to an image processor configured to generate a user-viewable image (not shown).

Many conventional telescopes 110 are commercially available and suitable for use with disclosed endoscopes. For example, telescopes having adequate image quality (e.g., resolution, contrast, etc.) typically have an outer diameter of about 4.0 mm. For example, a Model No. M3-30A, telescope, available from Gyrus ACMI, Inc., can be successfully used with disclosed endoscopes.

Another commonly used internal instrument is an electrode 111 (e.g., FIG. 23) having a working portion 161 positioned adjacent a distal end. The working portion, sometimes also referred to as an energizable element, e.g., an anode tip, can be configured to cut, ablate, abrade, vaporize, coagulate or fuse tissue, cauterize blood vessels and/or otherwise treat or manipulate a target site.

As noted above, an electrode can have a forked structure defining spaced apart first and second wire portions 160a, 160b. An energizable element 161 can be operatively coupled to the first and second wire portions.

The first and second wire portions 160a, 160b of the electrode 111 shown in FIGS. 22 through 24 can have substantially the same voltage potential as each other and can be electrically coupled to the energizable element 161, or anode tip. With such a configuration, the energizable element is sometimes referred to as a monopole, or a monopolar electrode. First and second conductive tubes 162a, 162b (e.g., stainless-steel tubes) can be positioned co-axially relative to the first and second wire portions 160a, 160b, respectively. The conductive tubes 162a, 162b can be electrically insulated from the wire portions 160a, 160b radially and electrically coupled to a grounding circuit portion (not shown). When a sufficient voltage potential is supplied to the first and second wire portions 160a, 160b, and thereby, to the anode tip, an arc can form between the anode tip and the conductive tubes 162a, 162b, forming an energized region in the space between the energizable element 161 and the tubes 162a, 162b. In some instances, such an arc can cause a plasma to form within the energized region.

The tubes 162a, 162b extend from the distal end 163 of the electrode 111 in a proximal direction, and can merge into a single joined tube 165 that extends to a contact region 166 adjacent the proximal end 164. The single joined tube 165 can be electrically coupled to a return contact 167 configured to electrically couple to the grounding circuit portion (not shown).

A power contact 168 can be positioned adjacent the proximal end 164 of the electrode 111. An energizeable and insulated power wire 169 can extend from the power contact 168, through the single joined tube 165, and split into the first and the second wire portions 160a, 160b extending through the corresponding first and second tubes 162a, 162b. The power contact 168 can electrically couple the power wire 169 to an external power source (not shown) configured to energize the power wire, and thereby, the anode tip 161.

A tubular insulator 170 can extend distally of the power contact 168 and electrically isolate the power contact 168 from the return contact 167, as shown in FIG. 24A. The insulator can be formed of any suitably dielectric or insulating materials, such as, for example, Radel R5100.

An electrode clip 115, or other retention member, can retain the elongate tube 165 in a sliding engagement with an inner sheath 108 (FIG. 1A). For example, a retention member can define an electrode engaging portion 119 configured to engage, e.g., by clamping or swaging, or otherwise join with, e.g., by welding or soldering, an exterior of the tubular electrode body. The retention member 115 can have opposed, flared tangs 117 (FIG. 23) being contoured as to be slideably engagable with an external contour of an inner sheath 108. With such a retention member, a proximal end 164 of the electrode 111 urged to and fro longitudinally along the inner sheath 108, the retention member 115 can slide longitudinally along the external surface of the inner sheath. In some instances, a suitable retention member 115 can be formed from a sheet material, such as, for example, stainless steel.

In other embodiments, the internal instruments 110, 111 can be other viewing instruments with other type of imaging devices, other treating instruments or manipulating instruments, such as, for example, a knife, a scissors, a forceps or a probe.

Fluid Flow Paths

As noted above, an internal instrument 110 positioned within the inner sheath 108 obstructs a portion of the cross-sectional area of the bore of the inner sheath and thereby reduces the available cross-sectional area of the inner sheath available to act as a fluid conduit 112 (FIGS. 1A, 2A). An inner sheath 108 having a mushroom-shaped contour (FIGS. 1A, 2A) provides opposed lobes 126a, 126b that allow a working fluid to bypass the obstruction caused by the internal instrument 110, 111. An opening at the distal end of the inner sheath 108 can allow a flow 114 of working fluid to exhaust from the inner sheath, providing an inflow opening 113 to a target site.

As also noted above, the exterior surface 116 of the inner sheath 108 is inwardly spaced from an interior surface 118 of the outer sheath 102, forming a gap 120 (FIG. 3A) through which a fluid can flow. In some instances, the inner sheath 108 and the outer sheath 102 have substantially constant cross-sectional profiles along their respective lengths. Accordingly, the gap 120 through which a fluid can flow remains substantially constant between a proximal end and a distal end of the conduit 122, providing an outflow opening 123 positioned at a distal end 104 and allowing fluid from a target site to be drained. As shown in section in FIG. 3A, the outflow opening 123 can be oriented transversely relative to a longitudinal central axis 124 of the outer sheath 102, which allows the outer sheath to have a substantially continuous outer surface free of perforations 223 (FIG. 34). As noted above, such a continuous outer surface can reduce patient trauma during insertion and extraction of the outer sheath. Flow through a transversely oriented outflow opening 123 can be adequate in many instances. Nonetheless, drainage flow can be increased, in some circumstances, by perforating the outer sheath (e.g., FIG. 34) to allow additional fluid to enter the gap 120 through the wall of the outer sheath 102.

Working Element

A working element 130 and related components will now be described with reference to FIGS. 4 through 21. The working element 130 comprises at least guide rails 132a, 132b, the actuator block 134, the rotatable element 150, the sheath adapter 140 and a handle portion 180. As briefly explained above, some components of the working element 130 can rotatably and/or slideably couple an outer sheath 102 to one or more other endoscope components. The innovative working elements disclosed herein provide several advantages, including the ability to reduce an outermost diameter of the outer sheath while retaining the ability to use relatively large internal instruments, such as, for example, a telescope having a 4 mm outer diameter.

Figure 26:
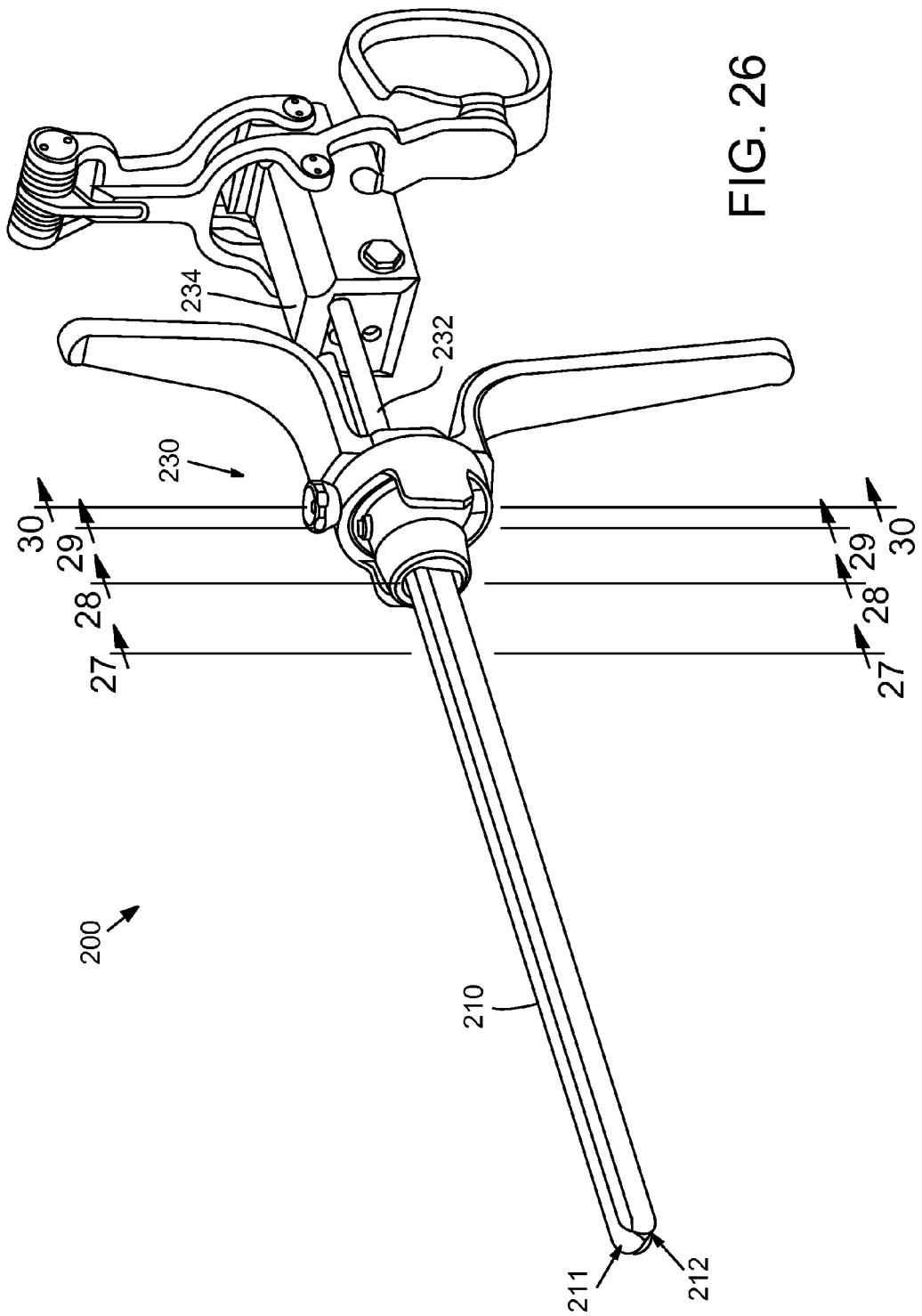
FIG. 26 is an isometric view of a portion of a second exemplary endoscope with the inner sheath and the outer sheath removed.

As shown in FIG. 2, the inner and outer sheaths 102, 108 extend distally of the working element 130. In FIG. 5, a distal end 152 (FIG. 12) of the rotatable element 150 of the working element 130 is shown, and FIG. 6 shows a section view of a main body 153 of the rotatable element 150. Opposed guide rails 132a, 132b extend proximally of the rotatable element 150, through the handle portion 180 (FIG. 7) and slideably support the actuator block 134 (FIG. 8). The actuator block 134 defines an instrument bore 135 through which at least one of the first and the second instruments 110, 111 can extend. The actuator block 134 can define one or more guide-rail bores 136 and each of the one or more guide rails 132a, 132b can extend through a corresponding one of the one or more guide-rail bores, such that the guide rails 132a, 132b laterally flank the first internal instrument 110 and the instrument bore 135. A longitudinal central axis of the guide rail 132a and a longitudinal central axis of the guide rail 132b are spaced from the first internal instrument 110 and the second internal instrument 111. The guide rails 132a, 132b can support the first and the second internal instruments 110, 111 as the actuator block 134 urges the internal instruments 110, 111 longitudinally along the outer sheath 102. Thick support structures for supporting internal instruments, such as, for example, thick-walled guide tubes surrounding an internal instrument, common in prior art instruments, can be eliminated by incorporating the guide rails 132a, 132b, allowing the first and the second internal instruments to be placed in close proximity to each other. Placing the instruments in close proximity to each other, in turn, can allow the use of instruments conventionally associated with larger outer sheaths. For example, a 4 mm telescope and an electrode conventionally associated with a 26 Fr (1 Fr equals 0.33 mm) outer sheath can be placed inside a 24 Fr gauge outer sheath. Placing instruments conventionally associated with larger outer sheaths in smaller outer sheaths provides less patient trauma while maintaining desired clinical performance. The first internal instrument 110 and the second internal instrument 111 can slideably extend through the handle portion 180, the rotatable element 150 and the sheath adapter 140. The first internal instrument 110 can slideably extend through the interior of the inner sheath 108 and the second internal instrument 111 can extend longitudinally along an exterior of the inner sheath between the inner sheath and the outer sheath 102. Alternatively, as shown in FIGS. 25, 26 and 30, the first and the second internal instruments 110, 111 can slideably extend through the interior of an inner sheath 208 and be supported by a rail 210 positionable within the inner sheath 208. With such a configuration, sliding the actuator block 134 longitudinally to and fro tends to urge the internal instruments to correspondingly move to and fro through a working stroke.

The working element 130 is configured to rotatably support the internal instruments 110, 111 such that the internal instruments are rotatable about a common axis of rotation. In the embodiment shown in FIGS. 1 and 2, the common axis of rotation is generally coextensive with the longitudinal central axis 124 of the outer sheath 102. In addition, the working element 130 is configured to fluidicly couple an interior of the inner sheath 108 to a supply of working fluid, and to fluidicly couple the conduit formed by the gap 120 between the inner sheath and the outer sheath 102 to a fluid drain (not shown).

Referring now to FIGS. 11 through 21, such a rotatable and sealed coupling will now be described. As shown in FIG. 22, a proximal end 105 of the outer sheath 102 can define a recessed region 103 configured to receive a distal sheath adapter 140 defining a longitudinally recessed region 140a and a working fluid inlet bore 158. The distal sheath adapter 140 can be fixedly coupled to the outer sheath 102. The outlet port 142 is fluidicly coupled to an interior of the outer sheath.

Figure 11:
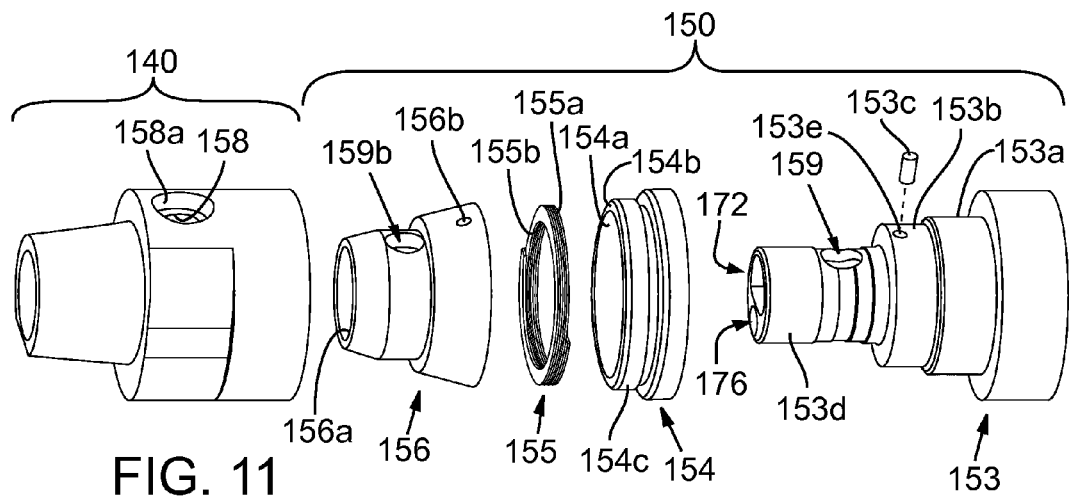
FIG. 11 shows an exploded view of an assembly of a rotatable element and a sheath adapter.
Figure 12:
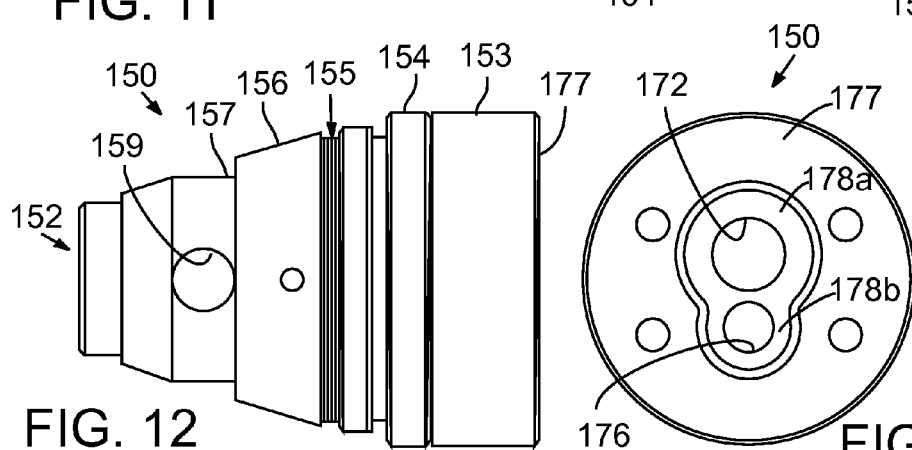
FIG. 12 shows a plan view from above a rotatable element shown in, for example, FIG. 22.
Figure 13:
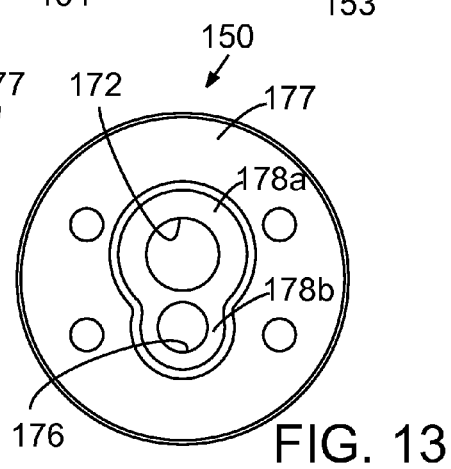
FIG. 13 shows an end-elevation view of the proximal end of the rotatable element shown in FIG. 12.
Figure 14:
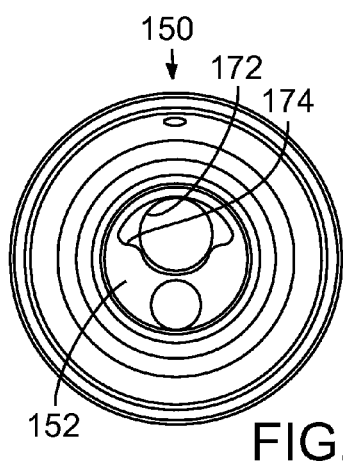
FIG. 14 shows an end-elevation view of the distal end of the rotatable element shown in FIG. 12.
Figure 15:
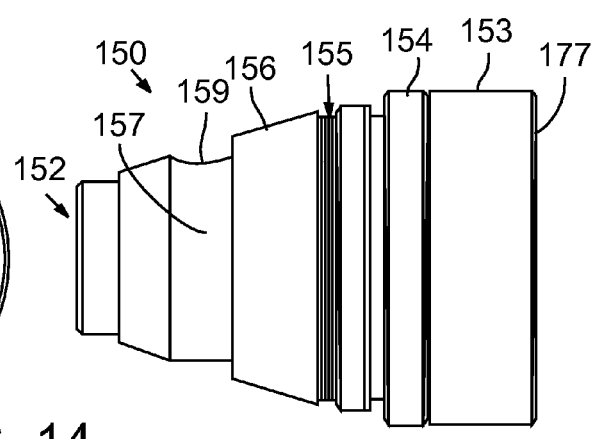
FIG. 15 shows a side-elevation view of the rotatable element shown in FIG. 12.
Figure 16:
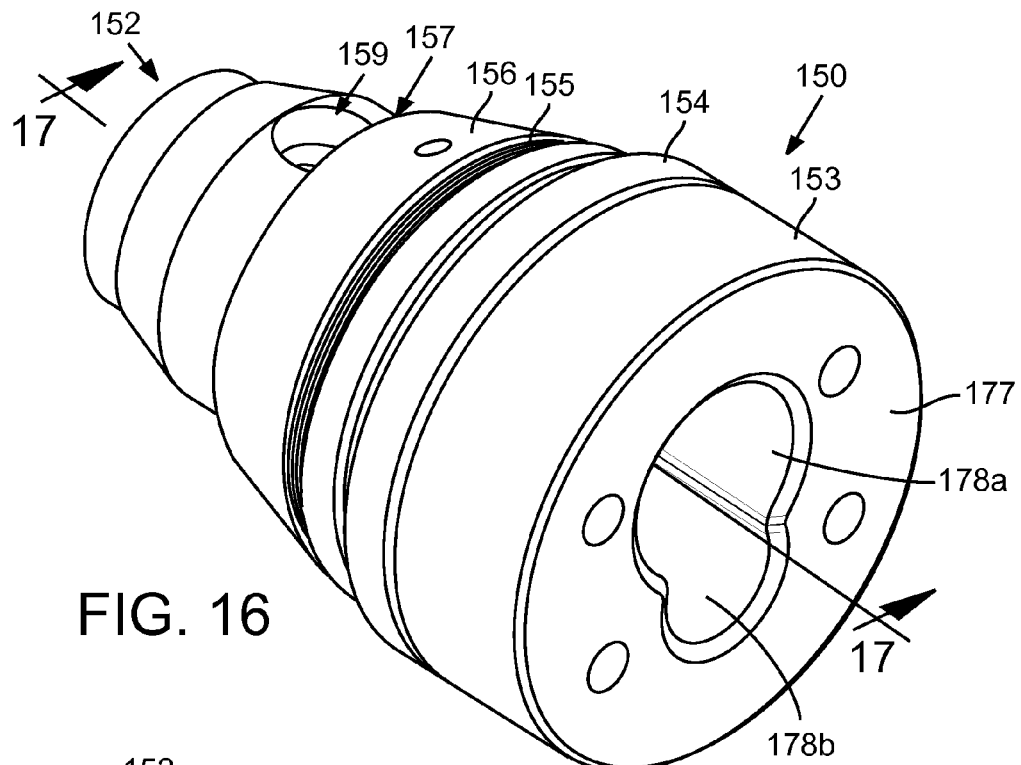
FIG. 16 shows an isometric view from above and to the left of the proximal end of the rotatable element shown in FIG. 12.
Figure 17:
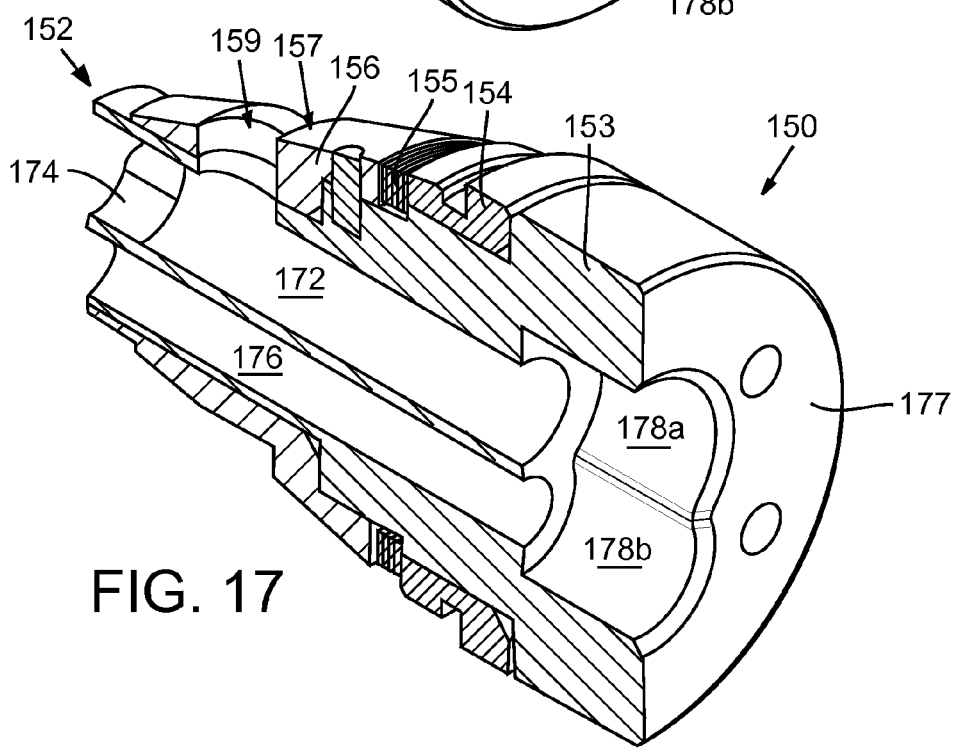
FIG. 17 shows an isometric view of the rotatable element shown in FIG. 12 sectioned along section 16-16 in FIG. 16.
Figure 18:
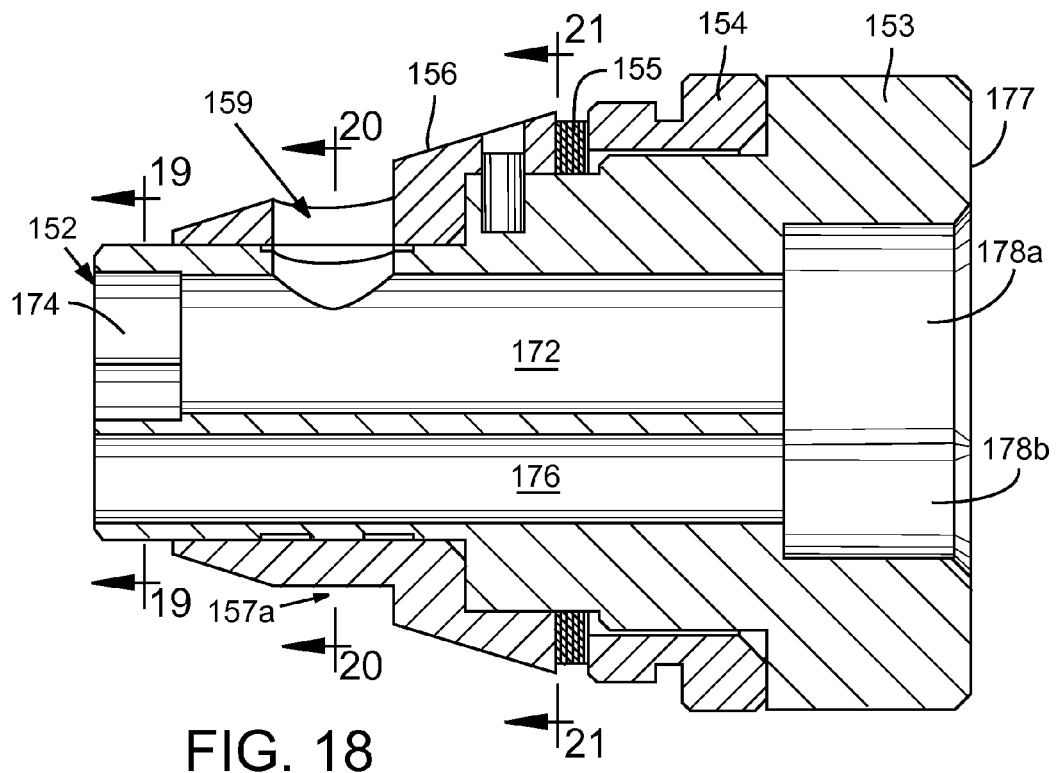
FIG. 18 shows a cross-sectional view of the rotatable element taken along section 16-16 shown in FIG. 16.
Figures 19, 20, 21:
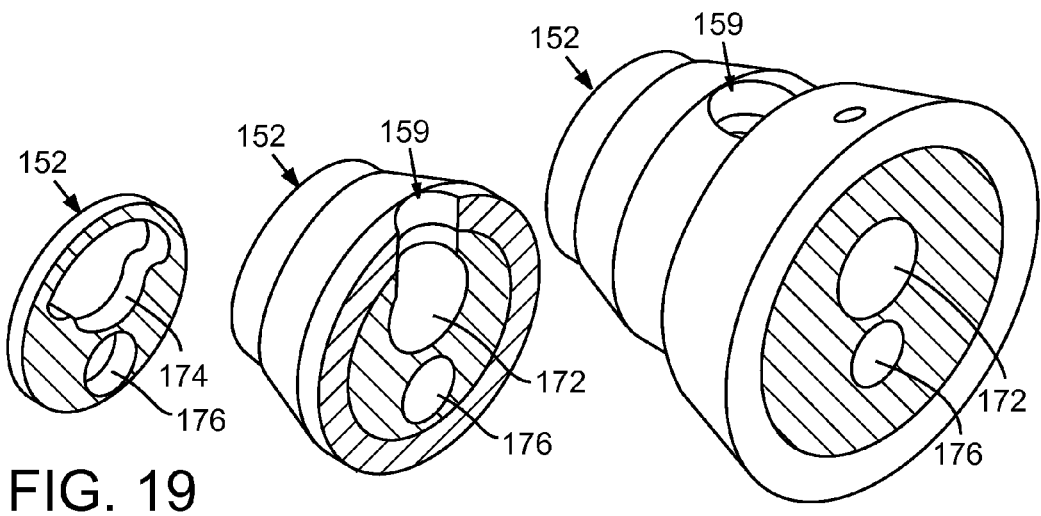
FIG. 19 shows a sectioned, isometric view of the distal end of the rotatable element shown in FIG. 12 from above and to the left of the proximal end of the rotatable element. A cross-section of the rotatable element taken along section 18-18 in FIG. 18 is visible in FIG. 19.
FIG. 20 shows a sectioned, isometric view of the distal end of the rotatable element shown in FIG. 12 from above and to the left of the proximal end of the rotatable element. A cross-section of the rotatable element taken along section 19-19 in FIG. 18 is visible in FIG. 20.
FIG. 21 shows a sectioned, isometric view of the distal end of the rotatable element shown in FIG. 12 from above and to the left of the proximal end of the rotatable element. A cross-section of the rotatable element taken along section 20-20 in FIG. 18 is visible in FIG. 21.

FIG. 11 shows an exploded view of an assembly of the rotatable element 150 and the sheath adapter 140. As shown in FIGS. 11, 16, 17 and 21, the rotatable element 150 comprises the main body 153, a ring 154, a spring 155, and a cone 156. The ring 154, the spring 155, the cone 156 can be assembled to the main body 153 and positioned around a circumference of the main body 153, such that the inner surface 154a of the ring is positioned radially outward of the shoulder 153a and the inner surface 155b of the spring 155 is positioned radially outward of the shoulder 153b. When the illustrated rotatable element 150 is assembled, the proximal face 155a of the spring 155 is in an opposed relationship to the distal face 154b of the ring 154. The illustrated ring 154 defines external thread 154c configured to threadably engage a corresponding internal thread defined by an inner surface of the distal adapter 140. A distal portion 153d of the main body 153 can be received within a bore 156a in the cone 156. A pin 153c can extend through a bore 156b in the cone 156 and into a bore 153e in the main body 153 to fixedly engage the cone and the main body. The recessed region 140a of the distal adapter 140 can receive the cone 156 (and the corresponding distal portion 153d of the main body 153) such that the cone 156 and the main body 153 can be rotated as one unit relative to the sheath adapter 140 and the ring 154. The rotatable element 150 can define a circumferentially-extending recess 157, or notch, (FIG. 12) such that a circumferentially extending channel 157a is defined between the rotatable element 150 and the distal sheath adapter 140 (FIG. 22).

The distal sheath adapter 140 can define a transverse bore (e.g., the illustrated working fluid inlet bore 158) extending inwardly from an external surface. The working fluid inlet bore 158 can be fluidicly coupled to a fluid inlet port 141 and to the circumferentially extending channel 57a. A bore 159a in the main body 153 and a bore 159b in the cone 156 together define a transverse bore 159 extending from the notch 157 to an instrument bore 172 in the main body 153, such that when the rotatable element 150 is assembled with the distal sheath adapter 140, the instrument bore 172 is fluidicly coupled to the fluid inlet port 141.

A distal end 152 (FIG. 14) of the rotatable element 150 can define a recessed region 174 configured to receive a proximal end of the inner sheath 108 (FIGS. 1 and 4) in a sealed, mating engagement between a periphery of the recess 174 and the outer surface 116 of the inner sheath 108. The inner sheath 108 is permanently attached to the recessed region 174 of the main body 153. The instrument bore 172 opens into the interior of the inner sheath 108, thereby fluidicly coupling the interior of the inner sheath to the fluid inlet 141.

The main body 153 of the rotatable element 150 can define a second instrument bore 176 extending substantially parallel to the first instrument bore 172. The second instrument bore 176 can be sufficiently spaced from the first instrument bore 172 such that the internal instrument 111 is positioned externally of the inner sheath 108 (FIGS. 1 and 4). Stated differently, a wall of the inner sheath 108 can be positioned between the first and the second instruments 110, 111.

Orienting the second instrument bore 176 substantially parallel to the first instrument bore 172 allows the corresponding first and second internal instruments 110, 111 to be moved longitudinally to and fro through a working stroke without one or the other of the instruments binding within the rotatable element 150. Such binding can occur when the respective instrument bores are not substantially parallel, particularly when one or both of the internal instruments are stiff (e.g., not sufficiently deformable to accommodate variations in spacing between the instruments, as would occur if the instrument bores are not parallel to each other). Electrodes 111 as disclosed herein can have a stiff body 165, and can be suitable for use with working elements as disclosed herein.

The illustrated working element 130 further comprises a grommet 151. The proximal face 177 of the rotatable element 150 defines a recessed region 178a, 178b configured to receive a grommet 151 having first and second bores 179a, 179b for sealingly and slidingly receiving the respective first and second internal instruments 110, 111. For example, the recessed region 178a, 178b has a "snow-man" shaped cross-section (FIG. 13) formed from the intersection of first and second cylindrically shaped recesses coaxially aligned with the respective first and second instrument bores 172, 176. As shown, the grommet 151 can be sandwiched, or positioned in compression, between the rotatable element 150 and the handle portion 180. The handle portion 180 is screwed to the rotatable element 150 so that the grommet 151 can be replaced.

The grommet 151 (shown in section in FIGS. 7 and 21) has a corresponding "snow-man" shaped outer contour configured to matingly engage the contour of the recessed region 178a, 178b. The grommet 151 can be integrally-molded so as to define a unitary construction from an elastic material, such as, for example, a high performance elastomer (e.g., a fluoroelastomer of the type commercially available under the brand Viton or Atlas) having a suitable coating to reduce friction. A grommet having a unitary construction can define first and second bores 179a, 179b. The distal end of one of the instrument bores 179a through the grommet 151 can define a lip 151a, or shoulder, extending radially inwardly from the circumference of the bore 179a. The lip 151a can sealingly mate with a corresponding outer surface of an internal instrument 110. The proximal end of the other of the instrument bores 179b can define a lip 151b, or shoulder, extending radially inwardly for sealingly mating with a corresponding outer surface of another internal instrument 111. In the illustrated embodiment, the lip 151a and the lip 151b are longitudinally spaced from each other along an insertion direction of the first and second internal instruments 110, 111. Providing longitudinally spaced lips 151a, 151b as just described can reduce friction between the grommet and the respective internal instruments, thereby further reducing the likelihood of binding the instruments when urging them through the working stroke.

Alternative Sheath Configuration

FIGS. 25 through 33 illustrate an alternative sheath configuration for an instrument 200 incorporating one or more innovative aspects of disclosed working elements. As with the working element 130 shown in FIGS. 4 through 21, internal instruments (not shown) can distally extend from the working element 230 parallel to each other.

In addition, a rail 210 extends distally from the working element 230. The rail 210 has opposed upper and lower channels 211, 212 configured to slideably receive a first internal instrument and a second internal instrument, respectively. The rail 210 can support the internal instruments, particularly where one or both of the internal instruments would likely buckle when urged to and fro through a working stroke (e.g., if either or both of the internal instruments are insufficiently stiff), or where one or both of the internal instruments is sufficiently flexible to bend if cantilevered from the working element. Some internal instruments can wind, at least partially, around the rail 210 or another of the internal instruments without one or both of the channels 211, 212.

An inner sheath member 208 can be positioned over the rail 210, as indicated in FIG. 31. As with the mushroom shaped inner sheath 108, an inflow opening 209 can be defined at a distal end 211 of the inner sheath 208. Nonetheless, since the inner sheath 208 shown in FIG. 31 is generally axisymmetric, an injected working fluid can exhaust from the inflow opening 209 with a substantially uniform velocity profile, in contrast to the exhaust from the opposed lobe regions 126a, 126b (FIG. 2A). In addition, the inner sheath 208 is generally larger than the contoured inner sheath 108 shown in FIG. 2A for receiving the first and the second internal instruments, as well as the rail 210, in the hollow interior.

An outer sheath 202 can be positioned over the inner sheath 208, as indicated in FIG. 31. Although the outer sheath 202 shown in FIG. 31 can have about the same outer diameter as the outer sheath 102 shown in FIG. 2, the gap between the larger inner sheath 208 and the outer sheath 202 is substantially smaller than the gap achieved by the configuration shown in FIG. 2. For example, the distal end of the inner sheath 208 has a flared outer portion 215 that can seal, or at least fill, any gap between the inner sheath 208 and the overlying outer sheath 202. Consequently, an outflow opening positioned solely at the distal end of the outer sheath 202 would induce too large an outlet loss (e.g., pressure drop) for many applications. To reduce such an outflow restriction, a distal portion of the outer sheath can be perforated, allowing the target site to drain through plural openings 223.

OTHER EMBODIMENTS

Incorporating the principles disclosed herein, it is to design and construct a wide variety of instruments configured for viewing treating, or otherwise manipulating regions normally obscured from view. Many such instruments can be of a smaller size than was previously attainable and thereby can reduce patient trauma and other related disadvantages of prior instruments. By way of example and not limitation, disclosed instruments can be used for endoscopes, including laproscopes, horoscopes, bronchoscopes, colonoscopes, gastroscopes, duoclenoscopes, sigmoiclo-scopes, push enteroscopes, choledochoscopes, cystoscopes, hysteroscopes, laryngoscopes, rhinolaryngoscopes, thorascopes, llrewroscopes, anhroscopes, canddas, neuroscopes, otoscopes and sinuscopes.

Although specific embodiments of internal instruments have been described, improvements to currently available internal instruments are contemplated in this disclosure. The innovations disclosed herein are compatible with improved (e.g., smaller) internal instruments. For example, an internal instrument having a smaller outer diameter could allow for a corresponding reduction in outer diameter of disclosed instruments.

This disclosure makes reference to the accompanying drawings which form a part hereof, wherein like numerals designate like parts throughout. The drawings illustrate specific embodiments, but other embodiments may be formed and structural changes may be made without departing from the intended scope of this disclosure. Directions and references (e.g., up, down, top, bottom, left, right, rearward, forward, etc.) may be used to facilitate discussion of the drawings but are not intended to be limiting. For example, certain terms may be used such as "up," "down,", "upper," "lower," "horizontal," "vertical," "left," "right," and the like. These terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" surface can become a "lower" surface simply by turning the object over. Nevertheless, it is still the same surface and the object remains the same. As used herein, "and/or" means "and" as well as "and" and "or."

Accordingly, this detailed description shall not be construed in a limiting sense, and following a review of this disclosure, those of ordinary skill in the art will appreciate the wide variety of imaging systems that can be devised and constructed using the various concepts described herein. Moreover, those of ordinary skill in the art will appreciate that the exemplary embodiments disclosed herein can be adapted to various configurations without departing from the disclosed concepts. Thus, in view of the many possible embodiments to which the disclosed principles can be applied, it should be recognized that the above-described embodiments are only examples and should not be taken as limiting in scope. I therefore currently claim as my inventions all that come within the scope and spirit of the following claims.

What is claimed:

1. An endoscope comprising:
a hollow outer sheath defining a longitudinal axis, and being configured for insertion into a patient's body;
a hollow inner sheath configured to slideably receive a first internal instrument, the hollow inner sheath being receivable within the hollow outer sheath; and
a working element configured to rotatably support at least the first internal instrument and a second internal instrument such that at least the first internal instrument and the second internal instrument are rotatable about a common axis of rotation being substantially coextensive with the longitudinal axis of the hollow outer sheath,
wherein the working element comprises at least one guide rail extending longitudinally along the common axis of rotation and an actuator block being slideably mountable to the at least one guide rail, the actuator block being so securable to at least one of the first internal instrument and the second internal instrument as to be able to urge the at least one of the first internal instrument and the second internal instrument longitudinally of the hollow outer sheath as the actuator block slides along the at least one guide rail,
wherein the hollow inner sheath is fixedly attached to the working element such that rotation of the working element causes rotation of the hollow inner sheath, the first internal instrument, and the second internal instrument,
wherein the hollow inner sheath is an axially asymmetric tubular structure along its length,
wherein the working element further comprises a grommet configured to sealingly receive the first internal instrument and the second internal instrument in respective first and second bores, and
wherein the first bore defines a first lip configured to urge against the first internal instrument and a second lip configured to urge against the second internal instrument, wherein the first lip extends radially inwardly from an outer circumference of the first bore and the second lip extends radially inwardly from an outer circumference of the second bore.

2. The endoscope of claim 1, wherein a longitudinal axis of the at least one guide rail is spaced from the first internal instrument and the second internal instrument.

3. The endoscope of claim 1, wherein the at least one guide rail comprises at least two guide rails positioned in a laterally flanking relationship relative to the first internal instrument.

4. The endoscope of claim 1, wherein the first lip and the second lip are longitudinally spaced from each other along an insertion direction of the first and second internal instruments.

5. The endoscope of claim 1, wherein the actuator block defines at least one guide-rail bore and the at least one guide rail extends through the at least one guide-rail bore.

6. The endoscope of claim 1, wherein the hollow inner sheath is rotatable within the hollow outer sheath such that the hollow inner sheath is configured to orbit within a bore of the hollow outer sheath about the common axis of rotation.

7. The endoscope of claim 6, wherein the hollow inner sheath is permanently attached to a part of the working element.

8. The endoscope of claim 1, wherein the working element further comprises:
an adapter element defining a longitudinally recessed region and a working fluid inlet bore; and
a rotatable element received in the longitudinally recessed region of the adapter element and defining a circumferentially-extending recess such that a circumferentially extending channel is defined between the rotatable element and the adapter element, wherein the rotatable element defines a transverse bore fluidicly coupled to the working fluid inlet bore and to the circumferentially extending channel, and wherein the rotatable element defines an internal instrument bore coupled to the transverse bore, wherein the internal instrument bore is fluidicly coupled to a bore through the hollow inner sheath, such that the working fluid inlet bore is fluidicly coupled to an interior of the hollow inner sheath.

9. The endoscope of claim 1, wherein the hollow inner sheath extends distally from the working element, and wherein the second internal instrument is positionable between the hollow inner sheath and the hollow outer sheath.

10. An endoscope comprising:
a hollow outer sheath defining a longitudinal axis, and being configured for insertion into a patient's body;
a hollow inner sheath configured to slideably receive a first internal instrument, the hollow inner sheath being receivable within the hollow outer sheath;
a working element configured to rotatably support at least the first internal instrument and a second internal instrument such that at least the first internal instrument and the second internal instrument are rotatable about a common axis of rotation being substantially coextensive with the longitudinal axis of the hollow outer sheath,
wherein the working element comprises at least one guide rail extending longitudinally along the common axis of rotation and an actuator block being slideably mountable to the at least one guide rail, the actuator block being so securable to at least one of the first internal instrument and the second internal instrument as to be able to urge the at least one of the first internal instrument and the second internal instrument longitudinally of the hollow outer sheath as the actuator block slides along the at least one guide rail,
wherein the second internal instrument is movably securable to the hollow inner sheath by a clip configured to slidingly engage the hollow inner sheath,
wherein the hollow inner sheath is fixedly attached to the working element such that rotation of the working element causes rotation of the hollow inner sheath, the first internal instrument, and the second internal instrument, wherein the hollow inner sheath is an axially asymmetric tubular structure along its length, and wherein the working element further comprises a grommet configured to sealingly receive the first internal instrument and the second internal instrument in respective first and second bores, and wherein the first bore defines a first lip configured to urge against the first internal, instrument, and a second lip configured to urge against the second internal instrument, wherein the first lip extends radially inwardly from an outer circumference of the first bore and the second lip extends radially inwardly from an outer circumference of the second bore.

11. The endoscope of claim 10, wherein the hollow inner sheath is axially asymmetric and the clip has a corresponding axially asymmetric contour positioned in sliding engagement with the hollow inner sheath.

12. The endoscope of claim 1, wherein the second internal instrument comprises an electrode assembly being positionable between the hollow inner sheath and the hollow outer sheath, and wherein the hollow outer sheath defines a distal portion comprising a ceramic coating, and wherein a plane defined by an outlet opening is not parallel to the longitudinal axis of the hollow outer sheath.

13. The endoscope of claim 1, wherein a gap between a distal portion of the hollow inner sheath and a distal portion of the hollow outer sheath defines an outlet opening of a fluid conduit configured to convey fluid from the patient's body, and wherein the second internal instrument comprises a distally positioned, energizable element being positionable within or adjacent to the outlet opening.

14. The endoscope of claim 13, wherein the hollow outer sheath defines a substantially cylindrically shaped outer surface free of any outlet openings of a fluid conduit configured to carry fluid away from a target site.

15. The endoscope of claim 10 wherein the working element further comprises an adapter element and a rotatable element having a main body and a recessed region in the main body and the hollow inner sheath is permanently attached to the recessed region of the rotatable element.

16. The endoscope of claim 1 wherein the hollow outer sheath further comprises:

an outer sheath distal portion integral to the hollow outer sheath and located where the hollow outer sheath first enters the patient's body;

an inner sheath distal portion integral to the hollow inner sheath and located where the hollow inner sheath first enters the patient's body;

wherein the inner sheath distal portion is flush with the outer sheath distal portion; and wherein the inner sheath distal portion has a straight and uniform cross section.

17. The endoscope of claim 16 wherein the outer sheath distal portion further comprises a dielectric material coating that coats the outer sheath distal portion both internally and externally.

* * * * *